United States Patent
Tverskoy

(10) Patent No.: US 9,675,250 B2
(45) Date of Patent: Jun. 13, 2017

(54) SYSTEM AND METHOD FOR MEASUREMENT OF VITAL SIGNS OF A HUMAN

(75) Inventor: Boris Tverskoy, Palo Alto, CA (US)

(73) Assignee: OXIRATE, Inc., Belmont, CA (US)

( * ) Notice: Subject to any disclaimer, the term of this patent is extended or adjusted under 35 U.S.C. 154(b) by 293 days.

(21) Appl. No.: 13/218,651

(22) Filed: Aug. 26, 2011

(65) Prior Publication Data

US 2012/0108928 A1    May 3, 2012

Related U.S. Application Data

(60) Provisional application No. 61/408,709, filed on Nov. 1, 2010.

(51) Int. Cl.
*A61B 5/1455* (2006.01)
*A61B 5/00* (2006.01)
*A61B 5/024* (2006.01)

(52) U.S. Cl.
CPC ........ *A61B 5/0059* (2013.01); *A61B 5/02416* (2013.01); *A61B 5/1455* (2013.01)

(58) Field of Classification Search
CPC .............. A61B 5/1455; A61B 5/14551; A61B 5/14532; A61B 5/0002; A61B 5/0059; A61B 5/14552
USPC ....... 600/310, 322, 323, 324, 326, 330, 331, 600/340, 344, 473, 476, 500; 356/41
See application file for complete search history.

(56) References Cited

U.S. PATENT DOCUMENTS

| | | | | |
|---|---|---|---|---|
| 4,114,604 A | * | 9/1978 | Shaw et al. | 356/41 |
| 4,180,784 A | * | 12/1979 | Nelson | H01S 3/104 |
| | | | | 372/26 |
| 5,632,272 A | * | 5/1997 | Diab et al. | 600/323 |
| 5,645,059 A | * | 7/1997 | Fein et al. | 356/41 |
| 5,807,267 A | | 9/1998 | Bryars et al. | |
| 5,921,921 A | | 7/1999 | Potratz | |
| 6,334,065 B1 | * | 12/2001 | Al-Ali et al. | 600/323 |
| 7,738,935 B1 | * | 6/2010 | Turcott | 600/336 |
| 2002/0038078 A1 | | 3/2002 | Ito | |
| 2004/0054269 A1 | * | 3/2004 | Rantala et al. | 600/322 |
| 2008/0161663 A1 | | 7/2008 | Lee | |

(Continued)

OTHER PUBLICATIONS

International Search Report from corresponding PCT/US2011/058066, filed on Oct. 27, 2011, mailed on Mar. 5, 2012.

*Primary Examiner* — Eric Winakur
*Assistant Examiner* — Chu Chuan (JJ) Liu
(74) *Attorney, Agent, or Firm* — Staniford Tomita LLP

(57) ABSTRACT

A method and system for optical measuring one or more vital signs of a human is described. The method includes generating an optical Pulse Width Modulated (PWM) signal modulated in accordance with a predetermined Pulse Width Modulation scheme. The PWM scheme includes one or more Pulse Width Modulations having different modulation frequencies. The method also includes applying the PWM optical signal to a measurement location in a blood perfused body tissue of the human and receiving light originated back from the measurement location. A photo current signal of a time response of the blood perfused body tissue to the PWM optical signal is indicative of the vital signs. The method includes generating a voltage signal from the photo current signal and processing the voltage signal for determining the vital signs.

35 Claims, 7 Drawing Sheets

(56) References Cited

U.S. PATENT DOCUMENTS

2009/0160364 A1* 6/2009 Ackermann et al. ......... 315/294
2009/0227853 A1   9/2009 Wijesiriwardana
2010/0016732 A1   1/2010 Wells
2011/0071373 A1*  3/2011 Li et al. ........................ 600/324

* cited by examiner

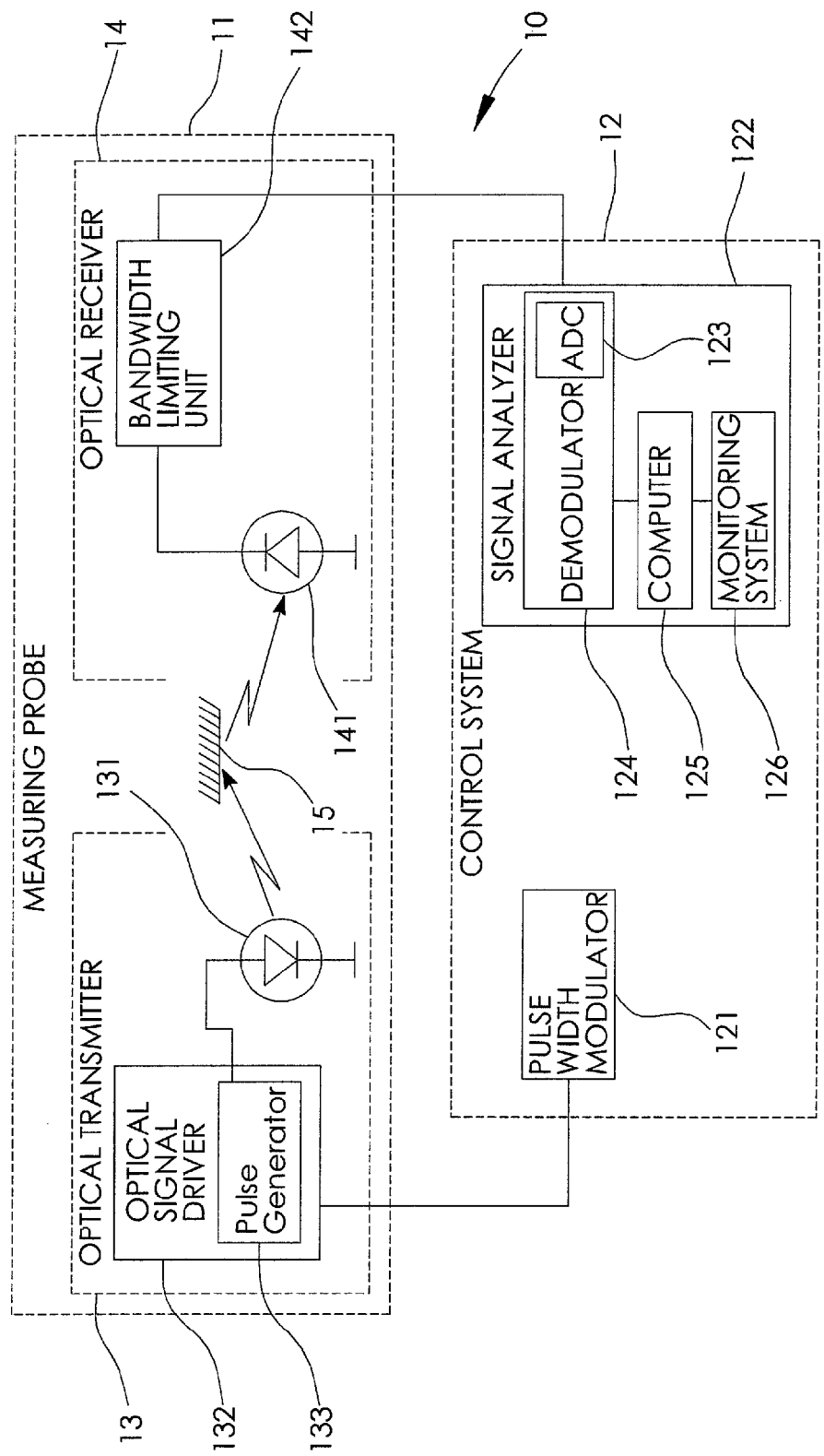

SYSTEM AND METHOD FOR MEASUREMENT OF VITAL SIGNS OF A HUMAN

CROSS-REFERENCE TO RELATED APPLICATIONS

This Application claims priority to U.S. Provisional Application No. 61/408,709 filed on Nov. 1, 2010, that is incorporated herein by reference in its entirety.

FIELD OF THE INVENTION

This invention relates to medical techniques for monitoring vital signs, and in particular, to a system and method for measuring vital signs by detecting light transmitted or reflected from a blood perfused body tissue.

BACKGROUND OF THE INVENTION

It is well known in the art to use light transmitted through or reflected from a medium in order to determine characteristics of the medium. For example, in the medical field, where non-invasive physiological monitoring of vital signs of a patient is often required, light transmitted through a portion of the body, and reflected or scattered from the body surface may be measured to determine information about the patient. This type of non-invasive measurement is comfortable for the patient and can be performed rather quickly.

For example, during surgery, blood pressure, heart rate, breathing rate and blood oxygen saturation are often monitored. Moreover, for some individuals, there may be a daily, even hourly need to measure such parameters to know the individuals health and/or to detect and treat some diseases.

Furthermore, information about vital signs can also be important to individuals involved in athletic training and physical exercising. For example, one of the important applications related to physical activity is continuous heart rate monitoring. This field still requires developments in a sense that a suppressive majority of nowadays optical sensors performing heart rate monitoring must be attached to body parts, which is inconvenient as well as relatively unreliable, mainly due to the dependency on motion-artifacts. Other kinds of related applications are related to blood pressure monitoring, oximetry, breathing rate monitoring, etc. All of these applications are an essential part of controlled physical activity, for example, in the process of heart rehabilitation. Accordingly, the most common requirement for all of the corresponding monitoring devices is the ability to be stable, compact, sensitive and reliable under operation with batteries.

A number of optical monitoring techniques have been proposed in the art that use light as an optical signal transmitted through a medium, such as a portion of a blood perfused body tissue with the goal of determining vital signs. Generally, such a monitoring system (also known as a photoplethysmograph) includes a transmitter utilizing a probe clipped on a part of the body (e.g., a finger, forehead, ear pinna or an earlobe) that includes an optical source, e.g., a light emitting diode (LED) or a laser, for irradiating the body part with light placed on one side of the of the body part while a photodetector is placed on an opposite side of the body part. Typically, the conventional systems operate with the optical signal that is either a continuous wave light or a train of optic pulses all having a constant repetition frequency and a constant width.

The monitoring system also includes a receiver utilizing an optical photodetector (e.g., a photo diode) positioned in an optical path so that it has a field of view which ensures the capture of a portion of the light which is transmitted, reflected or scattered from the body part. The optical detector converts the light (i.e., optical signal) into an analog electrical signal, which is subsequently amplified and provided to an analyzer to retrieve information that was present in the optical signal. The information present in the optical signal can be both the information inserted by the transmitter as well as the information about the medium.

An example of the medical monitoring device using light transmitted through a portion of the blood perfused body tissue is a pulse oximeter. Pulse oximetry is used to determine the oxygen saturation of arterial blood. Oxyhemoglobin mainly absorbs infrared light while deoxyhemoglobin mainly absorbs visible red light. Accordingly, pulse oximeter devices typically contain two types of light sources, either light emitting diodes or laser diodes, operating in the red band of light and in the infrared band of light, respectively. Pulse oximeter devices also include photo-detectors for each of above mentioned wavebands and the processing unit that detects the ratio of red/infrared absorption and calculates the patient's oxygen saturation of arterial blood.

Devices employing optical sensors to detect heart pulse rate are also known. For example, U.S. Pat. No. 5,807,267 describes a device that can be worn on the wrist. The device includes a LED producing a constant light output which is focused on the radial artery of a person. Pulsations of the radial artery (caused by the pumping action of the heart) cause the walls of the radial artery to expand and contract at the heart rhythm rate. These pulsations cause variations (modulation) in the amount of light being reflected from the surface of the artery to the photo sensitive surface of a photo transistor. The photo transistor converts the changes in the received light level to a varying electrical signal which is amplified and filtered. The filtered signal is then supplied to the analog-to-digital (A/D) converter and transformed into a digital word. The digital word is then processed into numerical results which are displayed on a liquid crystal display (LCD) as heart beats per minute.

The data provided to the analyzer that include not only information about vital signals but also various noise data. In particular, the sources of noise may be separated on two main groups, such as electrical noise, and optical noise. The electrical noise is naturally caused by the electrical circuits, whereas the optical noise includes natural light source noises, ambient light along with motion artifacts due to non-perfect optical coupling between the human body and the light source and the photo-detector.

Specifically, transmission of optical energy as it passes through the body is strongly dependent on the thickness of the material through which the light passes, or the optical path length. Many portions of a patient's body are typically soft and compressible. Therefore, when the patient moves, the thickness of material through which optical energy passes can change. This results in the changes of the optical path length. For example, if optical energy passes through a finger and the user of an optical device moves in a manner which distorts or compresses the finger, the optical path length changes. Changes in the optical path length together with the changes of venous blood movement through during motion can produce enough distortion in the measured signal to make it difficult or impossible to determine desired information.

Since a patient generally moves in an erratic fashion, the compression of the finger is erratic. This causes the change in optical path length to be erratic, making the absorption erratic, resulting in a difficult to interpret measured signal. Furthermore, in order to generate a strong output signal intensity, probes utilizing light transmitted though a medium are designed to maximize contact between the light source (e.g., LED) and the medium as well as the photodetector and the medium to promote strong optical coupling between the LED, the medium, and the photodetector. In this way, a strong, clear signal can be transmitted through the medium only when the body is generally motionless.

The artifacts produced by body motion can be concurrent with the heart pulse and detected by the sensor as noise. In some cases, this noise can produce signals of amplitude sufficient to completely mask the heart pulse signal which is to be measured. Accordingly, many prior art optical probes are designed for use only when a user (e.g., patient) is relatively motionless since, as discussed above, motion induced noise can grossly corrupt the measured signal.

Several attempts are known to design devices, which would operate with the light scattered from a portion of the user's body. Since thickness of the material reflecting the light affects the optical path length in the less extends then in the case when the light passes though the medium, these devices are less prone to motion artifacts. Nevertheless, in the case of the scattered light, the processing of the signal received by the photodetector is even more sophisticated task, due to a rather low signal-to-noise ratio resulting in a low stability of the monitoring. The physical explanation of this phenomenon is rather straightforward. Since the useful signal in the reflection/scattered geometry is based entirely on coming-back photons, these photons have to experience a lot of scattering acts and have a rather high probability to be absorbed on their way, and mainly forward scattering dominates. Accordingly, the angle of a single scattering is small, and a lot of scattering acts are required in order to increase the signal to noise ratio and maintain the receiver of the monitoring system in the dynamic range.

In this connection, the applicant is not familiar with any technique that provides robust data of vital signs by using scattered light measurements. For example, U.S. Pat. Appl. Pub. No. 2009/0227853 describes an ear hook plethysmography (PPG) sensor and/or pulse oximetry (SpO2) sensor that can be attached to the skin in the regions of superficial artery and vein and posterior auricular artery and vein around the ear. Accordingly, an ear wearable heart rate monitor can be constructed with these sensors. Although US2009/0227853 alleges that these sensor systems should be less vulnerable to motion artifacts under motion conditions such as running and exercising, this application does not describe, inter alia, how to eliminate the noise associated with the variations of optical coupling and the influence of an ambient light on the useful information signal.

SUMMARY OF THE INVENTION

There is a need in the art to provide a system for robust measurement of vital signs of a subject (e.g., human) that can be used in two related areas, such as clinical use and everyday monitoring of the subject's physical activities. In both these areas, miniaturization of the measuring devices is required in order to fabricate them wireless and cost effective, so that these measuring devices could be deployed to a large population.

Accordingly, there is a need in the art to provide a stable miniature stand alone system for robust measurement of vital signs of the user that will be less vulnerable to motion artifacts under user's motion conditions such as running and exercising. Moreover, it would be advantageous if the system will be less vulnerable to optical coupling between the user's body and the light source as well as between the user's body and the photo-detector.

It would be useful to have a system that can reliably operate not only with light transmitted though a portion of the user's body (i.e., in transmission mode), but also with the light reflected or scattered from the body part (i.e., in reflection mode). When a system can operate with the reflected or scattered light, rather than only with the transmitted light, such a system would be more comfortable for the user, since the measuring probe can be simply attached to a place on the body with the blood perfused body tissue, rather than be clipped on a part of the body.

Furthermore, the value of the reflected signal depends not only on variations of optical coupling, but also on the optical characteristics of the subject's skin vary from person to person. Likewise, these characteristics may vary in time even for the same person, depending on the state of his/her sweat glands, skin density, skin color, outside temperature, physical activity, etc.

The known way to cope with the limitation associated the variations of the optical coupling, characteristics of the patient's skin and the influence of an ambient light along with some other factors, is to provide an adaptive control by increase or decrease of the initial intensity of the light source by adjustment of the optical power emitted by the transmitter. In particular, when the power of the optical signal is too low to maintain the receiver within its linear dynamic range the intensity of the light source may be increased, while in the opposite case, when the power of the optical signal is too high, the intensity of the light source is decreased in order to maintain the receiver in its non-saturated dynamic range. However, the intensity adjustment may decrease the signal to noise ratio, because for the given geometrical configuration of the transmitter-receiver, the adjusted input light intensity can either easily fall below the sensitivity threshold of the receiver or saturate the receiver. Additionally, such adjustment of the light intensity may require substantial increase of the power consumption of the system. Accordingly, this solution of the problem associated with the inefficient power consumption makes such reflection-based photoplethysmographs non-practical.

The present invention satisfies the aforementioned needs in the art by providing a novel system and method for optical measuring vital signs of a subject. Example of the vital signs include, but are not limited to a heart rate, a heart rate variability, an arterial pulse waveform, a systolic blood pressure, a diastolic blood pressure, a mean arterial blood pressure, a pulse pressure, a breathing rate, a total hemoglobin content, and/or a blood oxygen saturation, etc. The present invention employs an adaptive control by applying a pulse optical signal to the subject and adjusting a width of the pulses of the applied signal. The adjusting can, for example, be carried out by using pulse width modulation in order to maintain the receiver in its non-saturated dynamic range. The receiver, preferably, should be maintained at the condition in which a linear part of the dynamic range has a substantial slope.

According to some embodiments, the input light intensity of the light source can be initially adjusted for the given geometrical configuration of light sources, light sensors, and the distances between them, and can be set to its optimal value suitable for the given user or a certain group of users. Then the intensity can be kept unchanged, whereas the average input light power of the light source during the measurements can be adjusted by employing one or more Pulse Width Modulations (PWM) of the optic signals emitted by the light source. In operation, depending on the instant conditions of the actual measurement, the values of the width and/or duty cycle of the pulses can be adjusted for each subject and even for the same subject.

The terms "pulse" and "series of pulses" are broadly used in the present description and the claims to describe pulse samples and any groups of the pulse samples in which the pulse samples can be assembled. Specifically, as will be described hereinbelow, the pulse samples (i.e., the pulses that have the shortest duration) can, for example, be assembled in such series of pulses as bursts of the pulse samples. In turn, the bursts can be assembled in such series of pulses as trains of the bursts.

According to some embodiments, the adaptive control of the system is implemented by a plurality of feedback loops for control of various parts of the receiver that may automatically perform the required adjustments of the average energy of light produced by the optical emitter(s) of the optical transmitter. These feedback loops can, for example, be employed in order to improve signal-to-noise ratio. Pulse Width Modulation (PWM) of the optical emitter is also an efficient way to get rid of noise signal associated with ambient light. Furthermore, PWM helps to decrease the influence on motion artifacts. According to the present invention, the amplifier can always be maintained within the non-saturated linear part of its characteristics by PWM, while the input intensity is maintained substantially constant at an optimal level Implementation of this PWM procedure can be digital, which does not require too much power consumption. When desired, the adaptive control may be patient-dependent, i.e., individually tuned.

According to some embodiments, an additional feedback loop can be provided to the system for power saving. For this purpose, the actual PWM frequency can be adjusted in accordance with the measured patient heart beats frequency.

According to some embodiments, the system generally comprises an optical transmitter, an optical receiver, a Pulse Width Modulator, and a signal analyzer.

The optical transmitter includes an optical emitter configured for generating and applying an optical signal to a measurement location in a blood perfused body tissue of the human. The optical transmitter also includes an optical signal driver including a pulse generator coupled to the optical emitter and configured for generating a series of electric pulses for driving the optical emitter by turning it "on" or "off".

The optical receiver includes an optical detector configured for receiving light originated back from at least a portion of the measurement location and generating a photocurrent signal including a time response of the blood perfused body tissue to the optical signal. The time response is indicative of the vital signs.

The bandwidth limiting unit is coupled to the optical detector. The bandwidth limiting unit has a predetermined gain and a predetermined bandwidth and configured for generating a voltage signal from photocurrent signal. The voltage signal is amplified to a desired gain level and has a desired band width.

The Pulse Width Modulator is coupled to the optical signal driver and configured for applying a Pulse Width Modulation (PWM) to the series of electric pulses in accordance with a predetermined Pulse Width Modulation scheme.

According to one embodiment of the present invention, the PWM scheme includes a Pulse Width Modulation having one predetermined modulation frequency.

According to another embodiment of the present invention, the PWM scheme includes two Pulse Width Modulations with two different modulation frequencies.

According to a further embodiment of the present invention, the PWM scheme includes three Pulse Width Modulations with three different modulation frequencies.

The signal analyzer is arranged downstream of the bandwidth limiting unit and configured for processing a voltage signal generated by the bandwidth limiting unit and determining the vital signs.

According to one embodiment of the present invention, the series of electric pulses after the two Pulse Width Modulations comprises repetitive bursts of electric pulse samples. Each burst has a predetermined burst duration time and a predetermined burst duty cycle. Moreover, each burst comprises a predetermined number of electric pulse samples having a predetermined pulse width and a predetermined pulse duty cycle. It should be noted that driving the optical emitter with shorter duration signals owing the pauses between the bursts results in the emitter being "on" for less time, resulting in less power consumption.

According to another embodiment of the present invention, the series of electric pulses after the three Pulse Width Modulations further comprises repetitive trains of bursts of electric pulse samples. In this case, each train of the bursts has a predetermined train duration time and train duty cycle and comprises a predetermined number of bursts having a predetermined burst duration time and a predetermined burst duty cycle. In turn, each burst comprises a predetermined number of electric pulse samples having a predetermined pulse width and a predetermined pulse duty cycle.

According to an embodiment, the optical emitter comprises one or more light emitting diodes.

According to an embodiment, the optical detector comprises one or more photodiodes.

According to an embodiment, the bandwidth limiting unit has a bandwidth with a corner frequency below the highest Pulse Width Modulation frequency.

According to an embodiment, the bandwidth limiting unit includes a transimpedance amplifier configured for amplifying and low pass filtering said photocurrent signal.

According to an embodiment, the transimpedance amplifier includes an operational amplifier.

According to an embodiment, the bandwidth limiting unit includes an additional low pass filter arranged downstream and coupled to the transimpedance amplifier. Preferably, but not mandatory, that a cut-off frequency of the additional low pass filter is positioned between a frequency of the variation of the measured vital sign and the highest frequency of the Pulse Width Modulation.

According to an embodiment, the bandwidth limiting unit includes a band pass filter arranged downstream and coupled to the transimpedance amplifier. Preferably, but not mandatory, that the band pass filter has a center frequency equal to a second frequency of the two (or three) Pulse Width Modulation scheme. The second frequency is lower than the highest frequency.

According to an embodiment, the signal analyzer includes a demodulator configured for processing the voltage signal generated by the bandwidth limiting unit for determining the vital signs.

According to one embodiment, the demodulator is a digital demodulator. The digital demodulator includes an A/D converter configured for converting the voltage signal generated by the bandwidth limiting unit from an analog form to a digital sampled form.

According to another embodiment, the demodulator is an analog demodulator.

According to an embodiment, the measuring system comprises a feedback controller coupled to the bandwidth limiting unit and to the Pulse Width Modulator.

According to one embodiment, the feedback controller is responsive to changes in a signal amplitude at an output of an amplifier of the bandwidth limiting unit. In this case, the feedback controller is configured to generate an amplifier gain control signal for controlling operation of the Pulse Width Modulator by adjusting the width and/or duty cycle of the pulses (e.g., pulse samples, and/or bursts assembled from the pulse samples), so as to maintain a gain level obtained at the output of the amplifier within an optimal range for operation of the amplifier.

When more than one modulation is applied, all the applied modulations have different modulation frequencies.

According to another embodiment, the feedback controller is responsive to changes in a signal amplitude at an output of a band pass filter of the bandwidth limiting unit. In this case, the feedback controller is configured to generate a filter control signal for controlling operation of the Pulse Width Modulator by adjusting the width and/or duty cycle of the pulses (e.g., pulse samples, and/or bursts assembled from the pulse samples) such as to maintain the signal amplitude at the output of the band pass filter within an optimal range for operation of the band pass filter.

According to a further embodiment, the feedback controller is responsive to changes of at least one modulation frequency of the employed Pulse Width Modulations of the predetermined Pulse Width modulation Scheme at an output of at least one unit of the bandwidth limiting unit selected from an amplifier, a low pass filter and a band pass filter. In this case, the feedback controller is configured to generate frequency control signals in order to match the frequency characteristics of the amplifier, the low pass filter and/or the band pass filter.

According to still a further embodiment, the feedback controller is responsive to changes in signal amplitude at an input of the demodulator. In this case, the feedback controller is configured to generate a detector control signal for controlling operation of the Pulse Width Modulator by adjusting the width and/or duty cycle of the pulses in order to maintain the signal within an optimal dynamic range required for operation of the demodulator.

According to still another embodiment, the feedback controller is responsive to the time response of the blood perfused body tissue to said optical signal. In this case, the PWM scheme always is used that includes three Pulse Width Modulations having three different modulation frequencies. The feedback controller is configured to generate a measurement time interval control signal in order to adjust the width and/or duty cycle of the Pulse Width Modulation of the trains of the bursts of the pulse samples, (i.e., the width and/or duty cycle of the pulses having the lowest frequency from said three PMW frequencies) to the variations of a heart rate of the subject.

The present invention also satisfies the aforementioned needs by providing a method for optical measuring at least one vital sign of a subject. The method comprises generating an optical Pulse Width Modulated (PWM) signal modulated in accordance with a predetermined Pulse Width Modulation scheme. The PWM scheme includes one or more Pulse Width Modulations having different modulation frequencies. The method further includes applying the PWM optical signal to a measurement location in a blood perfused body tissue of the human and receiving light originated back from the measurement location. A photo current signal of a time response of the blood perfused body tissue to the PWM optical signal is indicative of the vital signs. The method includes generating a voltage signal from the photo current signal and processing the voltage signal for determining the vital signs.

According to an embodiment, the generating of the voltage signal includes amplifying the voltage signal to a desired gain level and filtering the voltage signal to a desired band width.

According to an embodiment, the processing of the voltage signal includes converting the voltage signal from an analog form to a digital sampled form. Then, root mean square values of measured amplitudes of samples of the sampled voltage signal located in each period of the Pulse Width Modulation are calculated for one or several periods of the secondary Pulse Width Modulation that has a frequency lower than the highest frequency. Further, a discrete Fourier transform of the root mean square values is executed over said several periods. For obtaining a heart rate, the method also includes determining a major harmonic of the variations of the root mean square values. The applicant has found that this major harmonic represents a heart rate of the subject.

In the case when the PWM scheme includes three Pulse Width Modulations having three different modulation frequencies, the generating of the optical Pulse Width Modulated (PWM) signal can only be carried out during the measurement intervals defined by the lowest modulation frequency of these three Pulse Width Modulations.

According to an embodiment, the method further comprises adjusting the width and/or duty cycle of the pulses for at least one modulation of the employed Pulse Width Modulations having different modulation frequencies. The adjusting the duty cycle can be carried out either by an open loop control or a closed loop a feedback closed loop control.

The system and method of the present invention can be used for monitoring physical activity of individuals involved in athletic training and physical exercising as well as in various clinical applications. The monitoring of physical activity can, for example, include a continuous control of the heartbeat rate, the blood oxygen saturation, etc. When desired, it can be expanded by a blood pressure control and by an exhaled gas analysis, mutatis mutandis, to provide effective control of the aerobic level. In turn, the clinical applications may include distant monitoring of the patient state by wireless control of his heartbeats rate, heartbeats variability, the breath rate, and other signs.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 illustrates a schematic block diagram of a system for optic measurements of at least one vital sign of a subject, according to an embodiment of the present invention;

DETAILED DESCRIPTION OF THE PREFERRED EMBODIMENTS

Figure 2A:
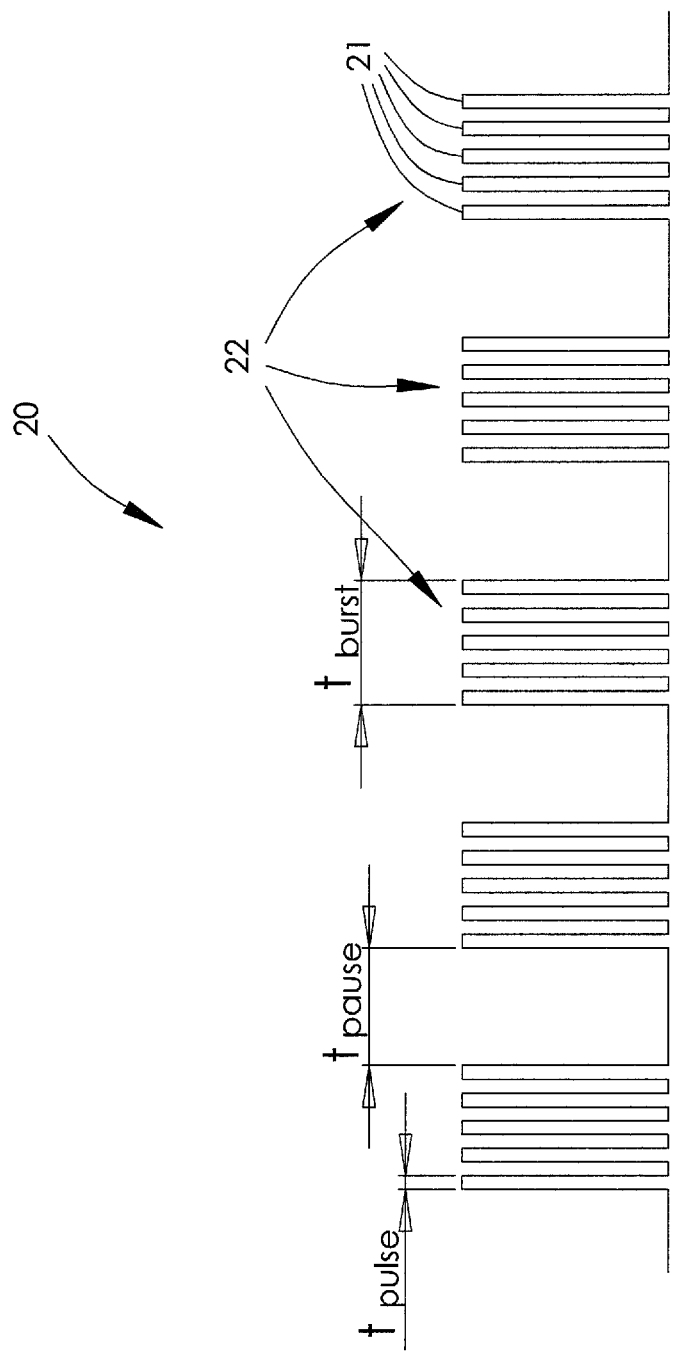
FIG. 2A shows an example of a timing diagram of a series of electric pulses generated by the optical signal driver of the system shown in FIG. 1 after Pulse Width Modulation.

The principles and operation of the system and method for measurement of at least one vital sign of a human according to the present invention may be better understood with reference to the drawings and the accompanying description, it being understood that these drawings and examples in the description are given for illustrative purposes only and are not meant to be limiting. The same reference Roman numerals and alphabetic characters will be utilized for identifying those components which are common in the system for measurement of at least one vital sign of a human and its components shown in the drawings throughout the present description of the invention. It should be noted that the blocks in the drawings illustrating various embodiments of the present invention are intended as functional entities only, such that the functional relationships between the entities are shown, rather than any physical connections and/or physical relationships.

Some portions of the detailed descriptions, which follow hereinbelow, are presented in terms of algorithms and/or symbolic representations of operations on data represented as physical quantities within registers and memories of a computer system. An algorithm is here conceived to be a sequence of steps requiring physical manipulations of physical quantities and leading to a desired result. Usually, although not necessarily, these quantities take the form of electrical or magnetic signals capable of being stored, transferred, combined, compared, and otherwise manipulated. In the present description, these signals can be referred to as values, elements, symbols, terms, numbers, or the like.

Unless specifically stated otherwise, throughout the description, utilizing terms such as "processing" or "computing" or "calculating" or "determining" or the like, refer to the action and processes of a computer system, or similar electronic processing device, that manipulates and transforms data.

Referring to FIG. 1, a schematic block diagram of a system 10 for optic measuring at least one vital sign of a subject (e.g., a living human) is illustrated, according to one embodiment of the present invention. Examples of the vital signs which can be measured by the system of the present application include, but are not limited to, a heart rate, a heart rate variability, an arterial pulse waveform, a systolic blood pressure, a diastolic blood pressure, a mean arterial blood pressure, a pulse pressure, a breathing rate, a blood oxygen saturation, total hemoglobin content and/or anaerobic threshold monitoring, etc. In some implementations, the vital signs can be determined from timing of arterial pulses, the amplitude and/or magnitude of arterial pulses, or from arterial pulse waveforms by using, for example, a Fourier analysis of the processed signal for one or more different wavelengths and obtaining a ratio of the predetermined functions of the corresponding Fourier components of the processed signal for various wavelengths, as will be described hereinbelow.

The system 10 comprises such main constructional parts as a measuring probe 11 and a control system 12 electrically coupled to the measuring probe 11. It should be noted that the control system 12 can be integrated with the measuring probe 11 in a unitary device. In this case, the control system 12 can be arranged either at the transmitter side or at the receiver side. Alternatively, the control system 12 can be located separately from the measuring probe 11. For example, the control system 12 can be integrated with a computer device (not shown), and communicate with the optical signal driver 132 arranged in the measuring probe 11 via electrical wires or via wireless transmission.

According to one embodiment of the present invention, the measuring probe 11 comprises an optical transmitter 13 and an optical receiver 14. The optical transmitter 13 includes an optical emitter 131 configured for generating and applying an optical signal to a measurement location 15 in a blood perfused body tissue of the human (not shown), and an optical signal driver 132 including a pulse generator 133 coupled to the optical emitter 131 and configured for generating a series of electric pulses for driving the optical emitter 131 by turning it "on" or "off".

According to some embodiments, the control system 12 is configured for adaptive control of the pulsed optical signal emitted by the optical transmitter 13 by adjusting at least a width of pulses of the pulsed optical signal in order to maintain the optical receiver 14 in its non-saturated dynamic range. Preferably, the optical receiver 14 should be maintained at the condition where a linear part of the dynamic range has a substantial slope.

According to some embodiments, the optical signal driver 132 is coupled to a Pulse Width Modulator 121 configured for Pulse Width Modulation (PWM) of the series of electric pulses generated by the pulse generator 133 in accordance with a predetermined Pulse Width Modulation scheme.

According to one embodiment of the present invention, the PWM scheme includes a Pulse Width Modulation having a predetermined modulation frequency. According to another embodiment of the present invention, the Pulse Width Modulation scheme includes two Pulse Width Modulations having different modulation frequencies. According to yet another embodiment of the present invention, the Pulse Width Modulation scheme includes three Pulse Width Modulations having three different modulation frequencies.

As shown in FIG. 1, the Pulse Width Modulator 121 is associated with the control system 12, i.e., separately from the measuring probe 11; however other implementations and configurations of the measuring system are also contemplated. For example, the Pulse Width Modulator 121 can be arranged at the transmitter side, whereas other elements of the control system 12 can be arranged separately from the Pulse Width Modulator 121. According to a further embodiment, the Pulse Width Modulator 121 can be arranged at the receiver side.

It should be understood that when the optical signal is rapidly switched on and off, due to Pulse Width Modulation, less energy is wasted at the transmitter side, when compared to the conventional techniques employing continuous wave regime for operation. Indeed, driving the optical emitter 131 with short duration signals results in the emitter being "on" for less time, and therefore with less power consumption.

In order to control the signal levels at the receiver side, the predetermined Pulse Width Modulation scheme of the present invention includes modulation at one or more modulation frequencies. The provision of the PWM at more than one modulation frequency provides assembling of the driving pulses in various groups.

The terms "pulse" and "series of pulses" are broadly used in the present description and the claims to describe pulse samples and any groups of the pulse samples in which the pulse samples can be assembled. Specifically, as will be described hereinbelow, the pulse samples (i.e., the pulses that have the shortest duration) can, for example, be assembled in series of such pulses as "bursts" of the pulse samples. In turn, the pulse bursts can be assembled in series of such pulses as "trains" of the bursts.

FIG. 2A shows an example of a timing diagram of a series 20 of the driving pulses generated by the optical signal driver 132 after applying two Pulse Width Modulations at different frequencies. As shown in this example, the driving pulses include pulse samples 21 which are assembled in repetitive pulse bursts 22. It should be understood that although for simplicity of illustration only five pulse samples 21 in each burst 22 and only five bursts 22 are shown in FIG. 2A, generally the pulse series 20 can include any desired number of the pulse samples in each burst and any desired number of the pulse bursts, depending on the duration of operation of the system. The bursts 22 have a burst repetition rate (burst modulation frequency), whereas the pulse samples 21 have a sample repetition rate (sample modulation frequency). Each pulse burst 22 contains a plurality of the driving pulse samples 21, and is separated from the neighboring burst by a pause tpause 23. Each pulse burst 22 contains a predetermined number Nsamples of pulse samples 21 and has a predetermined burst duration time tburst and a predetermined burst duty cycle Dburst. In turn, each pulse sample 21 has a predetermined sample width tsample and a predetermined sample duty cycle Dsample.

After the Pulse Width Modulation procedure, the series 20 of the modulated driving pulses (the bursts 22 of the pulse sample 21) is fed to the optical emitter 131, which in turn generates a PWM optic signal in accordance with the same Pulse Width Modulation scheme, as will be described hereinbelow with reference to FIG. 4A.

Driving the optical emitter 131 with modulated electric signals only during the pulse burst and being "off" during the pauses 23 between the bursts results in the optical emitter 131 being for less time or with less power consumption than the conventional systems in which the optical emitter operates in a continuous wave regime. It should be understood that this PWM scheme using two Modulations also more effective than the operation with the series of pulses having just one constant repetition frequency during the entire operation of the system without PWM. The PWM scheme using two Modulations is also more effective than the PWM scheme using only one modulation frequency.

The Applicant has found that such a combined type of Pulse Width Modulation with two different frequencies allows, inter alia, information to be effectively embedded in the signal received by the optical receiver 14, and also enables retrieval of this information. Such information can, for example, be the information embedded during the modulation of the pulse bursts 22 at the transmitter side. Likewise, the information can represent the changes in the characteristics of the transmission/reflection medium.

For example, when the medium is a blood perfused body tissue of a human, the information about variations of the amount of blood and the degree of red blood cell aggregation in the irradiated portion of the body can be embedded in the optic signal transmitted through (or reflected from) this medium. In turn, the variations of the amount of blood and the degree of red blood cell aggregation are modulated by the heart beats. Accordingly, the information about the rate of heart beats of the subject can be retrieved from the measured signal, as will be described herein below.

Moreover, such a combined type of Pulse Width Modulation can minimize the influence of ambient light on the signal received by the optical receiver 14, and accordingly to enhance the reliability of the detection. For example, when an optical path characteristic in the medium changes with a frequency of 10 Hz and an ambient light noise has a frequency of 120 Hz, the sample modulation frequency can be set to about 100 kHz, while the burst modulation frequency can be set to about 10 kHz.

It should be noted that the magnitudes of the PWM parameters depend on the type of vital signs selected for the measurements, skin color, sweat glands state, optical coupling quality, etc. For example, for measurements of heart rate, that can be varied in the range of 30 to 250 beats per minute, the modulation parameters can be set to the following values: tburst can be in the range of 10 microseconds-100 microseconds; Dburst can be in the range of 0.4-0.6; Nsamples can be in the range of 5-20; tsample can be in the range of 0.01 microseconds-10 microseconds; and Dsample can be in the range of 0.01-1.

Figure 2B:
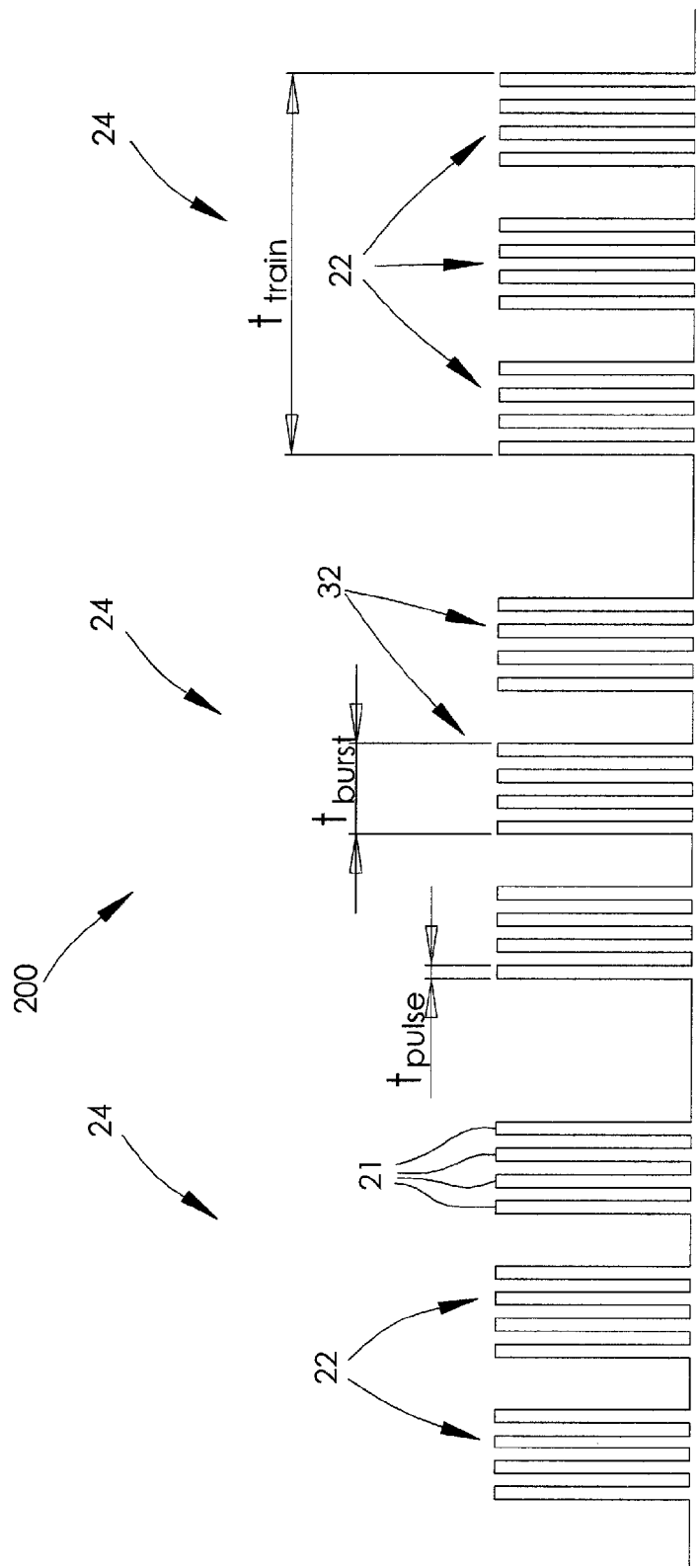
FIG. 2B shows another example of a timing diagram of a series of electric pulses generated by the optical signal driver of the system shown in FIG. 1 after Pulse Width Modulation.

FIG. 2B shows another example of a timing diagram of a series 200 of the driving pulses generated by the optical signal driver 132 after application of the Pulse Width Modulation scheme using three different frequencies. This example corresponds to the case when the pulse bursts 22 of the pulse samples 21 are further assembled in repetitive trains 24 of the bursts 22. It should be understood that although for simplicity of illustration only three trains 24 are shown in FIG. 2BA, generally, the pulse series 200 can include any desired number of the pulse trains, depending on the duration of operation of the system.

In accordance with this example, the modulated series 200 of the driving pulses further comprises repetitive trains 24 of bursts 22 of driving pulses 31. Each pulse train 24 of the pulse bursts 22 contains a predetermined number Nburst of pulse bursts 22 and has a predetermined train duration time ttrain and train duty cycle Dtrain. In turn, each burst 22 contains a predetermined number Nsamples of electric pulse samples 21 and has a predetermined burst duration time tburst and a predetermined burst duty cycle Dburst. In turn, each pulse sample 21 has a predetermined sample width tsample and a predetermined sample duty cycle Dpulse.

The applicant has found that employing the Pulse Width Modulation scheme having the assembling of the pulses as shown in FIG. 2B, can substantially reduce the need for gain control at the side of the receiver 14 of the measuring probe 11. Moreover, these modulation scenario further reduces the power consumption of the system when compared to the Pulse Width Modulation scheme shown in FIG. 2A (with the two pulse width modulations), since the measurements of the vital signs, and correspondingly the power consumption can be carried out only during the train duration time.

The magnitudes of the PWM parameters depend on the type of vital signs selected for measurements, skin color, sweat glands state, optical coupling quality, etc. For example, for measuring a heart rate varying in the range of 30 to 250 beats per minute, these parameters can be set to the following: ttrain can be in the range of 20 microseconds-400 microseconds; Dtrain can be in the range of 0.01-0.15; Nburst can be in the range of 2-5; tburst can be in the range of 10 microseconds-100 microseconds; Dburst can be in the range of 0.4-0.6; Nsamples can be in the range of 5-20; tsample can be in the range of 0.01 microseconds-10 microseconds; and Dsample can be in the range of 0.01-1. It should be noted that for this example the frequency of the PWM for the pulse samples is fixed and equal to 100 kHz. It means that the time period between the pulse samples is 10 microseconds.

Turning back to FIG. 1, the optical emitter 131 can include one or more optical sources, such as light emitting diodes (LEDs), laser diodes, or similar emitting devices (only one LED is shown in the present example), which are accommodated with respect to the subject such that the optical sources are dispersed along the surface of the subject's blood perfused body tissue. Having multiple emitters increases the likelihood that at least one of the emitters is positioned such that its signal can be received by the receiver. Furthermore, if light of all the emitters emitting the same optical signal is captured by the receiver, then the combined signal yields a greater signal at the receiver.

Depending on the vital sign selected for determination, the optical sources may, for example, operate all at the same light wavelength. According to another embodiment, at least one of the light sources operates at a different wavelength. For example, for measurements of heart rate, one or more light emitting sources can operate at the same wavelength that can be selected within the transparency window of hemoglobin and water, i.e. in the red-near infrared spectral range, such as 600 nm through 1000 nm. When the monitoring of total hemoglobin is targeted this range can be expanded till 1350 nm. Likewise, when it is necessary to control independently the variations of the optical coupling and the noise caused by the coupling variations, an additional wavelength can be from this window, e.g., around 400 nm.

For measurements of a level of oxygen saturated in blood, at least two types of light emitting sources operating in the red band of light and in the infrared band of light are required.

As shown in FIG. 1, the arrangement of the optical emitter 131 with respect to measurement location 15 is such that the system 10 operates with reflected light. However, the system 10 can also operate with transmitted light, mutatis mutandis.

According to one embodiment of the present invention, the optical receiver 14 includes an optical detector 141 configured for receiving light originated from (i.e., transmitted through or reflected from) at least a portion of the illuminated measurement location 15 of the subject (not shown), and for generating a photo current signal that includes a time response of the blood perfused body tissue to the applied optical signal. The time response is indicative of vital signs of the subject.

For example, the time response can be time variations of a channel parameter K(t) characterizing the optical pass loss and/or time variations of an effective optical attenuation coefficient.

Accordingly, the effective optical attenuation depends on the absorption and scattering of the applied light, and is modulated by the variations of the amount of blood and the degree of red blood cell aggregation in the irradiated portion of the body. In turn, the variations of the amount of blood and the degree of red blood cell aggregation are modulated by the heart beats. Accordingly, the information about the rate of heart beats of the subject as well as other vital signs can be retrieved from the measured time response of the subject's blood perfused body tissue, as will be described herein below.

It should be also understood that the time response of the blood perfused body tissue to the applied optical signal can depend on the optical coupling between the light source and the irradiated body portion and/or on the coupling between the optical detector and the irradiated body portion. Therefore, when the subject moves, for example during breathing, the optical coupling can change, and therefore will be modulated by the breathing frequency and by the frequency of other motion artifacts. Accordingly, the information about the frequency of breathing and some other motion artifacts can be inferred from the electric current signal produced by the optical detector 141.

It should also be noted that the time variance component of the signal is naturally smeared by the inevitable time variance component caused by noises originated from the electrical circuits, optical components, LEDs and photodiodes, as well as from fluctuations of the optical coupling between the transmitter, receiver and the body parts to which the transmitter and receiver are attached, motion artifacts, etc.

The optical detector 141 can include one or more photodiodes or other photo-receiving devices distributed along the surface of the subject's blood perfused body tissue and positioned in an optical path so that a field of view of the optical detector 141 ensures the capture of a portion of the light which is transmitted, reflected or scattered from the blood perfused body tissue. Using multiple detectors can result in a lower sensitivity of the system to the changes in orientation or position of the receiver and transmitter, since this provision provides a higher chance that the optical signal irradiated by the transmitter is received by the receiver.

An example of the suitable photodiode includes, but is not limited to, a common low-cost PN photodiode, a PIN photodiode, an avalanche photodiode (APD), phototransistor, a photothyristor, a photomultiplier tube (PMT), etc.

The optical receiver 14 also includes a bandwidth limiting unit 142 arranged downstream and coupled to the optical detector 141. The bandwidth limiting unit 142 is configured to convert the PWM photocurrent generated by the optical detector 141 into a high gain voltage signal and to ensure that the "on-off character" with the highest frequency of the Pulse Width Modulation is removed, so that only the lower frequency components of the Pulse Width Modulated signal are further processed for retrieving the information about the vital signs. Accordingly, the bandwidth limiting unit 142 has a predetermined gain and a predetermined bandwidth and is configured for processing the photocurrent signal fed from the optical detector 141 and generating an amplified and band width limited voltage signal. Preferably, the bandwidth limiting unit 142 has a bandwidth with a corner frequency below the highest Pulse Width Modulation frequency. In this case the bandwidth limiting unit can ensure that the on-off character of the Pulse Width Modulation is mainly removed.

Figure 3A:
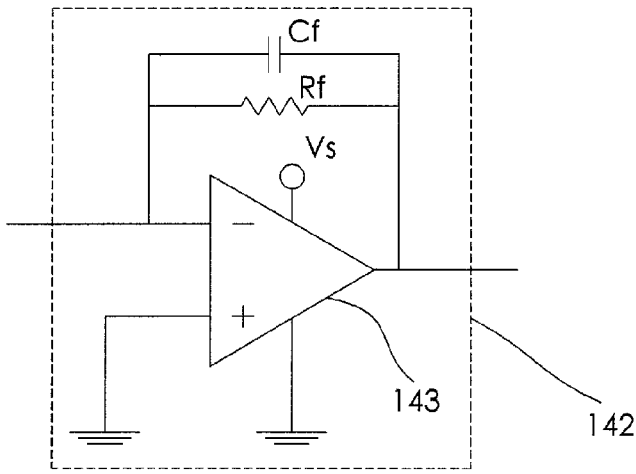
FIG. 3A illustrates a schematic block diagram of the bandwidth limiting unit of the system shown in FIG. 1, according to an embodiment of the present invention.

Referring to FIG. 3A, a schematic block diagram of an example of the bandwidth limiting unit 142 is illustrated. According to this example, the bandwidth limiting unit 142 is based on a transimpedance amplifier which includes an operational amplifier 143, however other implementations of the bandwidth limiting unit 142 are also contemplated. A resister RF and a capacitor CF are connected in parallel across the input and output of the operational amplifier 143. A gain of the operational amplifier is set by the resister RF. An output voltage VOUT of the operational amplifier 143 for low frequencies can be obtained by VOUT=−(IIN×RF), where IIN is the photocurrent signal generated by the optical detector 141. The capacitor CF is added to make the operational amplifier stable. Likewise, CF limits the bandwidth of the operational amplifier. Accordingly, the transimpedance amplifier acts as a low-pass filter.

In operation, the highest frequency of the received Pulse Width Modulated signal can be filtered out, while the low frequency component of the signal is amplified. The resulting signal will be indicative of the amplitude of the emitted optical signal, the duty cycle of the received Pulse Width Modulated optical signal and the changes in the medium, i.e., in the measured subject's blood perfused body tissue.

It should be understood that reliability of operation of the optical receiver 14 depends on the power of the optical signal. If the signal power generated by the optical detector 141 is too great, the operational amplifier 143 may become saturated; whereas if the signal is too weak, the further processing of the signal generated by the bandwidth limiting unit 142 may be not accurate. Therefore if the channel parameter K(t) or the effective optical attenuation coefficient is not a priori known, or when these characteristics of the medium change in time, there is a need to adjust the photo current IIN and/or the value of the resistor RF.

In order to address this issue, the present invention employs a predetermined modulation scheme which allows control over the emitted energy by adjusting the duty cycle of the optical emitter 131, and thus allowing control over the level of the signal fed to the bandwidth limiting unit 142 at the side of the optical transmitter 13. As will be explained below, the system of present invention can employ either an open-loop control or a closed loop control for the duty cycle adjustment.

Figure 3B:
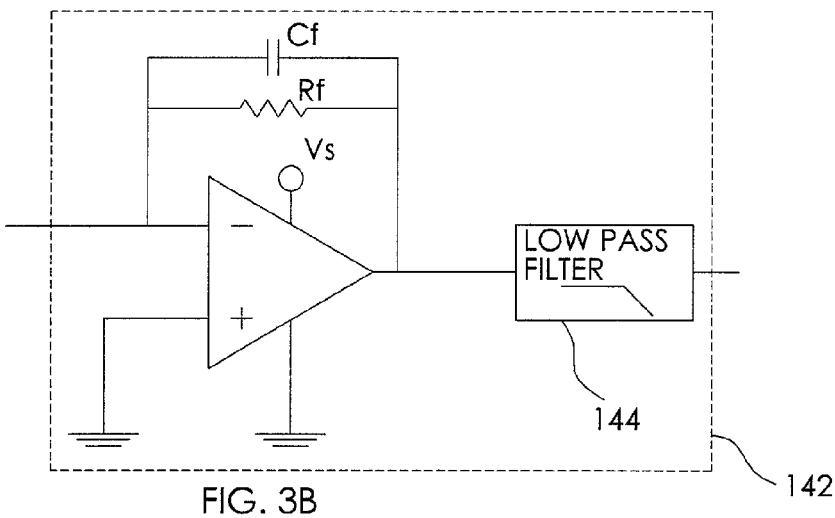
FIG. 3B illustrates a schematic block diagram of the bandwidth limiting unit of the system shown in FIG. 1, according to another embodiment of the present invention.

Referring to FIG. 3B, a schematic block diagram of another example of the bandwidth limiting unit 142 is illustrated. The bandwidth limiting unit shown in FIG. 3B differs from the bandwidth limiting unit shown in FIG. 3A in the fact that it further includes an additional low pass filter 144 coupled to the output of the operational amplifier 143. The additional low pass filter 144 can further filter out and/or reduce strong high frequency harmonics of the Pulse Width Modulation. In particular, this filter further removes the high frequency components of the PWM so that the low frequency information in the optical signal representing the relatively slow changes in the transmission channel is not disturbed by the modulation signal. The output of this filter depends on the duty cycle of the Pulse Width Modulation, thus allowing matching the dynamic range of the received signal to full dynamic range of the other elements of the system arranged downstream of the bandwidth limiting unit 142, such a demodulator and/or an A/D converter.

Filtering by the low pass filter 144 can be used in addition to (or instead of) the filtering that is provided by the operational amplifier 143. Accordingly, the low pass filter 144 can only be the low pass filter in the signal path of the receiver, when, instead of the operational amplifier 143, some other current-to-voltage converter is used without the low pass filtering feature, e.g., having the bandwidth that exceeds the highest frequency of the Pulse Width Modulation. It should be understood that the cut-off frequency of the low pass filter 144 can best be positioned between the frequency of the information signal to be observed and the highest frequency of the Pulse Width Modulation. For example, when the measuring system of the present application is configured for measuring heart rate being in the range of 30-250 beats per minute and the pulse frequency used in the Pulse Width Modulation Pulse being 10 kHz, the cut-off frequency of the low pass filter 144 can, for example, be set to 100 Hz.

Figure 3C:
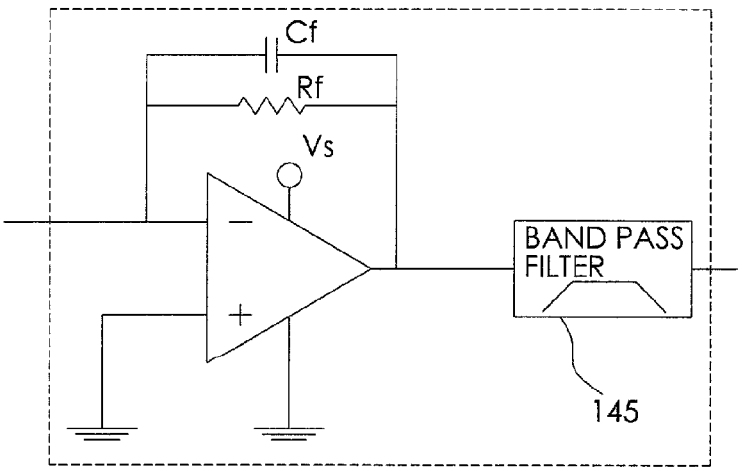
FIG. 3C illustrates a schematic block diagram of the bandwidth limiting unit of the system shown in FIG. 1, according to a further embodiment of the present invention.

Referring to FIG. 3C, a schematic block diagram of a further example of the bandwidth limiting unit 142 is illustrated. The bandwidth limiting unit shown in FIG. 3C differs from the bandwidth limiting unit shown in FIG. 3B in the fact that the additional low pass filter 144 is replaced with a band pass filter 145 coupled to the output of the operational amplifier 143. According to an embodiment, the band pass filter 145 has a center frequency equal to the frequency of the burst modulation (see FIG. 2A). Accordingly, the band pass filter 145 removes all of the signal components except those with the frequency of the burst modulation, which allows robust detection of the information embedded itself in the burst modulation. This information can be either the information embedded in the burst modulation by the transmitter, or represent the changes in the characteristics of the transmission medium.

It should be noted that owing to band pass filter 145 the signal is free from ambient noise while the signal's amplitude depends on PWM duty cycle. In other words, the provision with the band pass filter 145 provides both adjustment of the signal level to suit the electronic circuitry of the receiver and concurrently offers the advantage of rejecting disturbances.

Turning back to FIG. 1, the control system 12 also includes a signal analyzer 122 arranged downstream of the bandwidth limiting unit 142 and configured for processing the voltage signal generated by the bandwidth limiting unit for determining one or more vital signs. The signal analyzer 122 includes a demodulator 124 for processing and converting the data to one or more vital signals.

According to one embodiment, the demodulator 124 is a digital demodulator configured for performing digital demodulation using the digital representation of the received signal provided by the A/D converter. The digital demodulator includes an analog-to-digital converter (ADC) 123 arranged downstream of the bandwidth limiting unit 142 and coupled thereto through a suitable electronic interface block (not shown). The A/D converter 123 is operable to convert the signal provided by the bandwidth limiting unit 142 from an analog form to a digital sampled form.

According to another embodiment of the present invention, the demodulator 124 is an analog demodulator configured to perform analog demodulation by using any known technique, such as an envelope detector, etc.

The demodulator 124 can be associated with a suitably programmed computer system 125 having, inter alia, such known utilities as a processor (not shown), a memory unit (not shown) for storing the processed data, and a monitoring system 126 configured for presenting the measured results of vital signs. The processor is preprogrammed by a suitable software model capable of analyzing the received data (i.e., output information signal of the A/D converter) and determining one or more desired vital signs. Accordingly, the processor can perform a number of data processing steps, calculations, or estimating functions, some of which will be discussed hereinbelow. It should also be understood that the present invention contemplates a computer program being readable by the computer system 126 for executing the method of the invention. The invention further contemplates a machine-readable memory tangibly embodying a program of instructions executable by the machine for executing the method of the invention.

The measured information (e.g., a heart rate, oxygen saturation, etc.) can be transmitted to the monitoring system 126 via electrical wires or via wireless transmission. The monitoring system 126 can include a display, printer and/or other monitoring devices (not shown). When desired, the monitoring system 126 can include an alarm system to produce a human detectable signal when a vital sign measurement generated by the output unit meets predetermined criteria. For example, the monitoring system 126 can be adapted to create a visual or audio alarm to alert a user that a detected vital sign is outside of a predetermined range. When desired the computer system 125 can be associated with other computer system, which are connected to each other through a network, for example, through the Internet, thereby to transmit the measured information about the vital signs to a desired party.

Figure 4A:
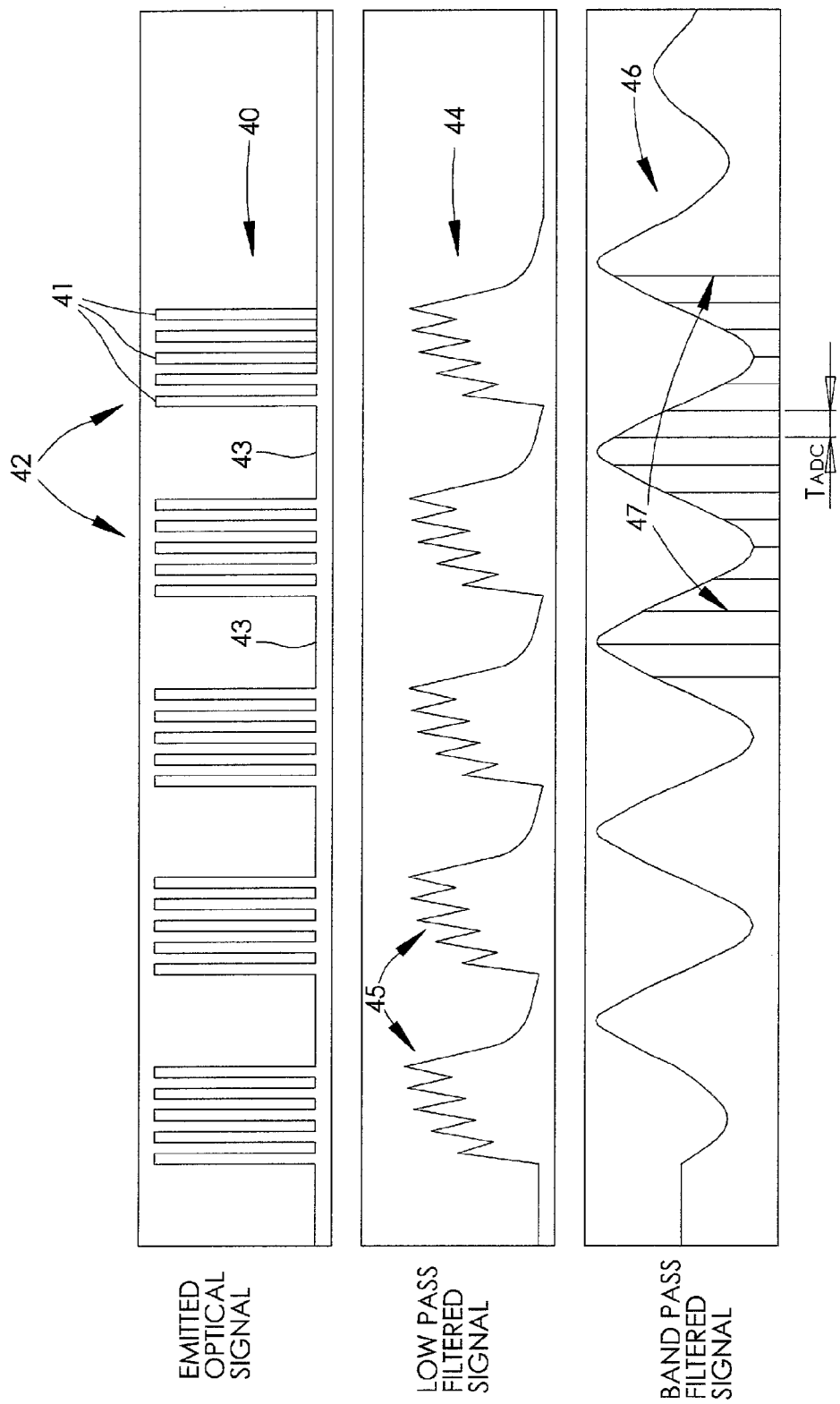
FIG. 4A illustrates an example of a timing diagram of the signals within the measuring system of the present invention.

Referring to FIG. 4A, an example of a timing diagram showing the timing relationships between the signals within the measuring system of the present invention is illustrated. The upper trace represents the optical signal 40 emitted by the optical transmitter 13. The optical signal 40 correspond to the series 20 of the driving pulses shown in FIG. 2A, which are generated by the optical signal driver 132 after applying two Pulse Width Modulations at two different frequencies.

According to this example, the optical signal 40 has a Pulse Width Modulated wave form and includes PMW pulse samples 41 modulated with a first (highest) PWM frequency. The PMW pulse samples 41 are assembled in repetitive PMW bursts 42 (for simplification of the picture only five bursts are shown), which are separated from each other by pauses 43 owing to the modulation with the second PWM frequency. It should be understood that the second PWM frequency is lower than the first PWM frequency.

The middle trace represents a bandwidth limited signal 44 as obtained at the output of the operational amplifier (143 in FIGS. 3A, 3B and 3C). As can be seen, a small part of components 45 corresponding to the highest frequency of the Pulse Width Modulation are still present in signal 44, whereas the main part of these components has been removed owing to the limited bandwidth of the operational amplifier 143, since it acts as a low pass filter. The secondary PMW frequency is fully present in the signal.

The lower trace represents a filtered bandwidth limited signal 46 obtained after the band pass filter (145 in FIG. 3C). As can be seen, all the highest frequency components 45 are removed. The filtered bandwidth limited signal 46 is then relayed to the input of the demodulator (124 in FIG. 1) for demodulation and for retrieving the vital signs.

The signal sampled by the A/D converter (123 in FIG. 1) of the demodulator (124 in FIG. 1) is shown by a reference numeral 47. The sampled signal is characterized by a sampling period. For example, when a frequency of the burst (i.e., secondary) modulation is in the range of 10 kHz, the sampled period TADC can be in the range of 1 MHz.

It should be noted that continuous repeating of the bursts 42 is not desired, since it results in waste of energy. Thus, the bursts 42 of the Pulse Width Modulated signal 40 need only be repeated as long as required for providing a stable sampled signal during the measurement interval, as indicated in FIG. 4A by the sampling period TADC of the measurement in the lower trace.

According to one embodiment, determining the changes of the optical pass characteristic K(t) occurring in the medium (e.g., blood perfused body tissue) owing to the time variant changes of either an arterial blood volume or erythrocyte aggregation state, can be done by taking A/D converted samples 47 corresponding to several periods of the burst modulation and calculating root mean square values for the measurement of amplitudes of the samples during each burst period, to with:

$$\text{Signal}_{RMS} = ([(\text{ADCsample}_1)^2 + (\text{ADCsample}_2)^2 + \ldots + (\text{ADCsample}_N)^2]/N^{1/2},$$

where N is the number of the samples 47 in one burst period or in a group of several close to each other burst periods. It should be understood that the optical signal 40 generally may includes any desired number of the burst, depending on the duration of operation of the system (although for simplicity of illustration only five bursts 42 are shown in FIG. 4A). Accordingly, the mean square values of the amplitudes of the samples 47 can be calculated for those busts which are far away from each other. For example, when a frequency of the burst modulation is in the range of 10 kHz and the sampled period can be in the range of 1 MHz, each M-th burst (where M can, for example, be between 1 and 1000) can be selected for the calculation of $\text{Signal}_{RMS}$.

It should be noted that the ADC samples should be evenly distributed across the period of the burst modulation and the sampling frequency must satisfy the Nyquist rate, and be more than twice of the frequency of the burst modulation. The sampling should continue for on e or more full periods. It should be noted that oversampling, i.e. taking more samples than the minimum required b the Nyquist frequency, can further improve the signal to noise ratio.

The burst frequency (i.e., secondary PWM frequency) should be substantially greater than the natural frequencies of the expected fluctuations of K(T). The fluctuations of the optical pass characteristic K(t) can be obtained from variations of the magnitudes of $\text{Signal}_{RMS}$ during the measuring time interval that includes several separated burst periods.

The Applicant has found that when a blood perfused body tissue of a human is measured, a frequency value of the major harmonic of the variation of the magnitudes of $\text{Signal}_{RMS}$ can represent a heart rate of the user of the measuring system. Accordingly, in order to obtain the heart rate, the processor of the system can, for example, execute a discrete Fourier transform of the $\text{Signal}_{RMS}$ data (i.e., $F[\text{Signal}_{RMS}(t)]$, where F denotes the operator of the Fourier transform) over several burst periods and obtain the major harmonic of $F[\text{Signal}_{RMS}(t)]$.

For measurements of a level of oxygen saturated in blood, the similar measurements can be carried out at least for two different wavelengths in the red band of light and in the infrared band of light. For each these light bands the entire procedure of the heart rate measurement is performed in order to obtain $\text{Signal}_{RMS\ i}(t)$ data corresponding to various wavelength, where the index i corresponds to a particular wavelength $\lambda_i$.

Further, for example, a ratio of predetermined functions of the magnitudes of the major Fourier component of the root mean square values over several periods for two various wavelengths can be calculated and used for calibration versus an arterial blood oxygen saturation rate of the subject.

When desired, a calibration plot or table can be created for a further determination of the level of oxygen saturated in the blood.

For example, a ratio $\text{Log}(\text{major}\{F[\text{Signal}_{RMS\ 1}(t)]\})/\text{Log}(\text{major}\{F[\text{Signal}_{RMS\ 2}(t)]\})$ can be calculated for two various wavelengths $\lambda_1$ and $\lambda_2$, and calibrated versus the arterial blood oxygen saturation rate of the subject, where major $\{F[\text{Signal}_{RMS\ 1}(t)]\})$ and $\text{major}\{F[\text{Signal}_{RMS\ 2}(t)]\})$ are the magnitudes of the major Fourier component of the signal $\text{Signal}_{RMS\ 1}(t)$ and $\text{Signal}_{RMS\ 2}(t)$, respectively. Such calculations are known per se, and are not expounded herein in detail. Applicants found that such a calibration can be rather stable for such a couple of wavelengths as 635 nm and 940 nm, although other pair of wavelength can also be used.

The same procedure performed for a different set of wavelengths, for example, 850 nm and 1300 nm can provide a calibration versus total blood hemoglobin value. In this case, the important limitation on the selection of the wavelengths is to select one of the wavelengths slightly out of the typical window of water transparency or at least at its boundary. Applicants found that the wavelength 1300 nm can, for example, be suitable for determination of total blood hemoglobin value of a subject.

In order to monitor heart rate variability (HRV) of a subject, the procedure of the heart rate measurement can be performed during the series of rather long time intervals, e.g. a few minutes or even longer. Then, for both the long-term and the short-term recordings such parameters as a mean heart rate, a standard deviation of the mean heart rate and a root mean square deviation of the heart rate can be calculated.

According to one embodiment, the HRV is calculated as a mean square deviation of the heart rate calculated over several partially overlapping time intervals.

According to another embodiment, the HRV is calculated as a mean square deviation of the heart rate calculated over several non-overlapping time intervals, each interval involving one or several more full heart bit cycles.

Some extra parameters can be calculated specifically for long-term recordings. These time-domain parameters are mainly associated with the overall variability of the HRV over the measuring time. However, the root mean square deviation of the heart rate is associated with fast (parasympathetic) variability.

It should be noted that the HRV measurement can be performed also in frequency-domain. This procedure is very informative because the HRV at certain frequency ranges can be associated with certain physiological processes. A known spectral analysis routine can be applied to the recording for the particular wavelength and the following parameters evaluated during 5-10 minute time interval: a Total Power, a High Frequency, a Low Frequency and a Very Low Frequency of the HRV. These frequency bands can be defined as follows. The high frequency band reflects parasympathetic tone and fluctuations caused by spontaneous respiration known as respiratory sinus arrhythmia. It is evaluated in the range from 0.15 Hz to 0.4 Hz.

In the range from 0.04 Hz to 0.15 Hz the low frequency power spectrum can be evaluated. This band can reflect both sympathetic and parasympathetic tone. The very low frequency power spectrum is evaluated in the range of 0.0033 Hz to 0.04 Hz. It is considered representing sympathetic tone as well as slower humoral and thermoregulatory effects. Monitoring of these changes is important in both clinical applications and control of physical activities.

It should also be noted that when the continuous monitoring of heart rate, HRV, and blood oxygen saturation rate is combined with an exhaled gas analysis for a particular person, it can be correlated with the personal aerobic threshold that is the key parameter of controlled physical activity.

Figure 4B:
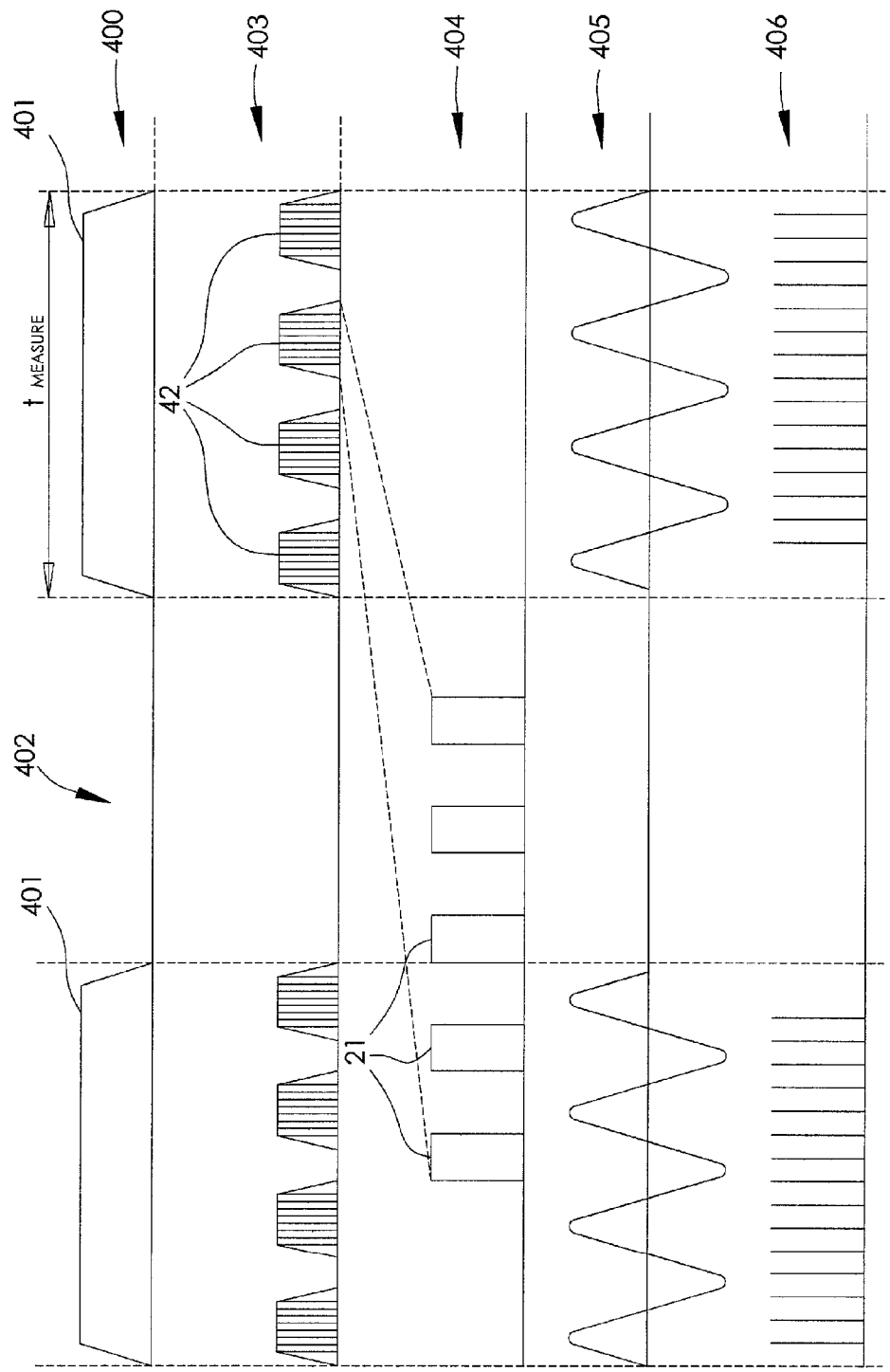
FIG. 4B illustrates another example of a timing diagram of the signals within the measuring system of the present invention.

Referring to FIG. 4B, another example of a timing diagram showing the timing relationships between the signals within the measuring system allowing obtaining further powers saving is illustrated. This example corresponds to the series 200 of the driving pulses shown in FIG. 2B, which are generated by the optical signal driver (132 in FIG. 1) after applying three Pulse Width Modulations at three different frequencies.

The upper trace (indicated by a reference numeral 400) shows the measurement intervals 401 of the measuring system of the present invention. According to this example, in order to save energy consumption, measuring is performed only during the measurement intervals 401. In this case, the optical transmitter (13 in FIG. 1), or at least the optical emitter (131 in FIG. 1), is turned off in pauses 402 between any two measurement intervals 401.

The second (from the top) trace (indicated by a reference numeral 403) represents the optical signal emitted by the optical emitter (131 in FIG. 1). This optical signal corresponds to the repetitive trains (24 in FIG. 2B) of the bursts 22 of the pulse sample 21, which are generated by the optical signal driver (132 in FIG. 1) after applying three Pulse Width Modulations at three different frequencies. Thus, the second trace 402 corresponds to the upper trace shown in FIG. 4A. According to this embodiment the optic pulses are assembled in the burst 42 and generated during the burst time periods.

The third (from the top) trace (indicated by a reference numeral 404) shows an enlargement of such an on-period for one burst 42 of the pulse samples 21. It should be understood that the pulse samples 21 have the highest modulation frequency, whereas the PWM trains 401 have the lowest modulation frequency.

The forth trace (indicated by a reference numeral 405) shows the output of the bandwidth limiting device (142 in FIG. 1), where the highest Pulse Width Modulation frequency has been removed by filtering and where, after the band pass filter (145 in FIG. 3C), only the fundamental frequency of the burst (intermediate) modulation remains. This signal is relayed to the input of the A/D converter (123 in FIG. 1). The fifth trace 406 shows the output of the A/D converter.

The fluctuations in amplitude of this intermediate frequency represent variation of K(t), and from these fluctuations one can derive the variations in transmission medium characteristics, for example a heartbeat signal, oxygen levels in the blood or other vital signs.

According to one embodiment, determining the changes of the optical pass characteristic K(t) occurring in the medium (e.g., blood perfused body tissue) owing to the time variant changes of either an arterial blood volume or erythrocyte aggregation state, can be done by taking A/D converted samples from the trace 406 corresponding to several periods of the burst modulation for each train 401 and calculating root mean square values for the measurement of amplitudes of the samples during the burst period for each train, to with:

$$\text{Signal}_{RMS} = ([(\text{ADCsample}_1)^2 + (\text{ADCsample}_2)^2 + \ldots + (\text{ADCsample}_N)^2]/N)^{1/2},$$

where N in this case is the number of the samples in one burst period or a group of several burst periods located within a pulse train. For instance, the last burst of each train can be selected for calculation of the root mean square values ($Signal_{RMS}$). Likewise, any other burst or a group of several bursts can be selected for calculation $Signal_{RMS}$. The calculated value of $Signal_{RMS}$ can be assigned to the corresponding train. Further these calculated values of $Signal_{RMS}$ for several trains can be used for calculating vital signs as described above with reference to FIG. 4A, mutatis mutandis.

The frequency of the measurement intervals 401 (in other words, the duty cycle Dtrain of the trains 24 in FIG. 2B) can be adjusted to the frequency of the variations of the optical pass characteristic K(t) to be measured. Accordingly, when K(t) corresponds to a heart beat signal, the repetition rate of the measurement periods 401 can be increased when the heartbeat rate increases. Likewise, when heartbeat rate decreases, the repetition rate of the measurement periods 401 can be decreased, thus further saving the consumption energy.

For example, when the heart rate is in the range of 30 beats per minute, the period of the measurement intervals 401 can be in the range of 0.01 seconds-0.03 seconds, whereas the heart rate is in the range of 250 beats per minute the period of the measurement intervals 401 can be in the range of 2 milliseconds-4 milliseconds.

It should be noted that the Pulse Width Modulator 121 employed in the system 10 shown in FIG. 1 provides an open loop control of the level of the signal fed to the bandwidth limiting unit 142, since the predetermined modulation scheme of the present invention allows controlling the emitted energy by adjusting the duration of pulsed operation and/or the duty cycle of the optical emitter 131. For example, when the modulated series of the pulse samples (31 in FIG. 2B) are assembled in repetitive trains comprising bursts of the pulse samples, the open loop control generally allows adjustment of at least one parameter selected from selected from the sample width, the sample duty cycle, the burst width, the burst duty cycle, the train width and the train duty cycle.

However, since the open loop control used in the measuring system shown in FIG. 1 does not use feedback, such an open-loop system cannot correct any errors in the PMW control. It also may not compensate for disturbances in the system. It is therefore would be advantageous to arrange the PMW control in an automatic way by using the feedback from the output of the bandwidth limiting unit 142.

Figure 5:
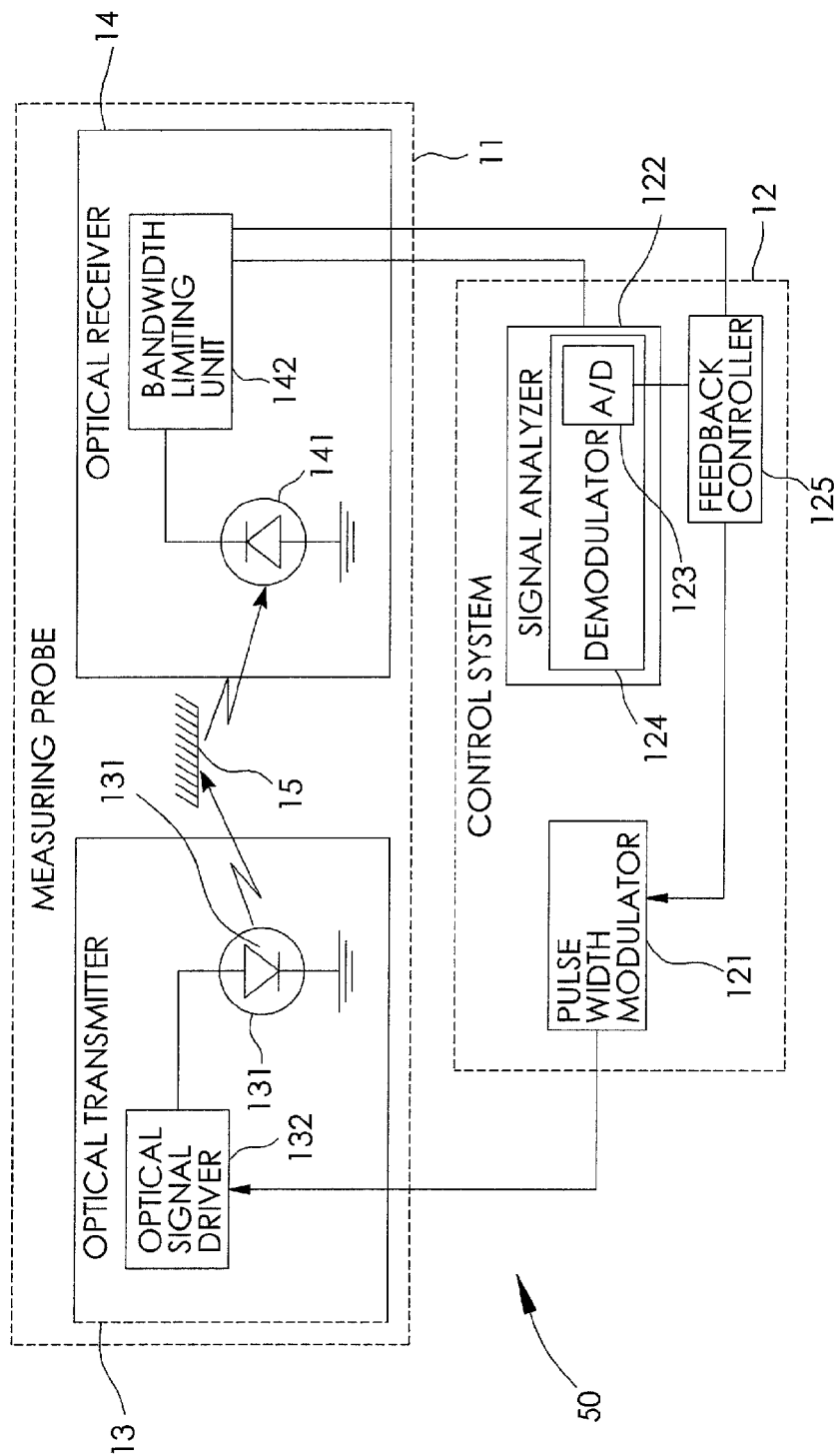
FIG. 5 illustrates a schematic block diagram of a system for optic measuring at least one vital sign of a subject, according to another embodiment of the present invention.

Referring to FIG. 5, a schematic block diagram of a measuring system 50 that uses a feedback to improve PMW control for optic measuring at least one vital sign of a subject is illustrated, according to an embodiment of the present invention. The system 50 differs from the system (10 in FIG. 1) in the fact that it employs a closed loop control by providing a feedback between the bandwidth limiting unit 142 and the Pulse Width Modulator 121.

As shown in FIG. 5, the system 40 includes a feedback controller 125 coupled to the bandwidth limiting unit 142 and to the Pulse Width Modulator 121. The feedback controller 125 can be implemented on the basis of a microcontroller circuit, but any other form of feedback, including implementation in analog hardware such as voltage to frequency converters are also contemplated. When desired, the feedback controller 125 can utilize the A/D converter 123. Alternatively, the feedback controller 125 can include a dedicated A/D converter (not shown).

The present invention employs an adaptive control by using a predetermined pulse width modulation scheme in order to maintain the receiver in its linear dynamic range of the non-saturated region. According to some embodiments, the input light intensity of the optical transmitter 13 can be initially adjusted for the given geometry of light sources of the optical emitter 131, optical detector 141, and the distances between the optical emitter 131 and optical detector 141, and set to its optimal value suitable for the given user or a certain group of users. Then, the intensity can be kept unchanged, whereas the average input light power of the light source can be adjusted during the measurements by employing one or more pulse width modulations (PWM) of the optic signals emitted by the light source. As described above, the pulsed signals can of the type of modulated pulse samples. Likewise, the pulse samples can be assembled in modulated bursts of pulse samples, which in turn can be assembled in modulated trains of pulse bursts. In operation, depending on the instant conditions of the actual measurement, the values of the width and/or duty cycle of the pulses (pulse samples, pulse bursts and pulse trains) can be adjusted for each user from various users, and even for the same user.

According the embodiment shown in FIG. 5, the adaptive control of the system is implemented by a plurality of feedback loops for control of various parts of the optical receiver 14 that may automatically perform the required adjustments of the average energy of the light injected by the optical emitter (s) of the optical transmitter 13. These feedback loops can, for example, be employed in order to improve signal-to-noise ratio. PWM of the optical emitter is also an efficient way to get rid of noise signal associated with ambient light. Furthermore, PWM helps to decrease the influence on motion artifacts. The bandwidth limiting unit 142 can always be maintained within the linear part of its characteristics by using a suitable PWM scheme, while the input intensity can be maintained constant at an optimal level Implementation of this PWM procedure is digital, which does not require too much power consumption. When desired, the adaptive control may be patient-dependent, i.e., individually tuned.

According to an embodiment, the feedback controller 125 is, inter alia, responsive to the changes in the signal amplitude at the output of an amplifier (e.g., the transimpedance amplifier 142 in FIGS. 3A-3C) of the bandwidth limiting unit 142, and configured to generate an amplifier gain control signal for controlling operation of the Pulse Width Modulator 121 in order to maintain a gain level obtained at the output of the amplifier at an optimal (reference) range for operation of the amplifier. Specifically, by adjusting the sample width and/or duty cycle, the amplifier of the bandwidth limited unit can be maintained in the optimal range below the saturation, i.e. where a linear part of the dynamic range has a substantial slope. This condition is required in order to have a suitable value of the signal-to-noise ratio. It should be understood that the adjusting of the burst width and/or burst duty cycle can enhance the value of the signal-to-noise ratio.

For example, if the optical path characteristic K(t) of the medium 15 is such that the level of the received optical signal results in saturation of the amplifier, the feedback controller 125 is configured to generate the amplifier gain control signal for controlling operation of the Pulse Width Modulator 121 in order to bring the gain level obtained at the output of the amplifier back to the reference (optimal) range. In this case, the control is performed by decreasing at least one parameter of the Pulse Width Modulations selected from the sample width, the sample duty cycle, the burst width and/or the burst duty cycle.

According to another embodiment, the feedback controller 125 is, inter alia, responsive to the changes in the amplitude of the signal at the output the band pass filter (145 in FIG. 3C) of the bandwidth limiting unit 142. In this case, the feedback controller 125 is configured to generate a filter control signal for controlling operation of the Pulse Width Modulator 121 in order to keep an amplitude of the filtered bandwidth limited signal (46 in FIGS. 4A and 4B) obtained after the band pass filter (145 in FIG. 3C) at a desired level. In particular, the control of the operation of the Pulse Width Modulator 121 can be carried out by adjusting at least one parameter of the Pulse Width Modulations selected from the sample width, the sample duty cycle, the burst width and/or the burst duty cycle.

According to a further embodiment, the feedback controller 125 is, inter alia, responsive to the changes of the signal amplitude at the input of the demodulator 124 and/or A/D converter 123. In this case, the feedback controller 125 is configured to generate a detector control signal for controlling operation of the Pulse Width Modulator 121 in order to keep the amplified received signal within the dynamic range of the demodulator 124 and/or A/D converter 123. By adjusting at least one parameter of the Pulse Width Modulations selected from the sample width, the sample duty cycle, the burst width and/or the burst duty cycle, the input signal of the A/D converter 123 or the modulator 124 can be kept in the optimal range for operation of the demodulator 124 and/or A/D converter 123.

Accordingly, if the A/D converter or the modulator reaches saturation, this is detected and the duration and/or the duty cycle of the Pulse Width Modulated Optical signal can be lowered, reducing the energy content. On the other hand, if the output of the amplifier is low, resulting in under utilization of the dynamic range and the resolution of the A/D converter, the amplifier gain and the signal levels at the input of the A/D converter can be brought back into the optimal range by increasing at least one parameter of the Pulse Width Modulations selected from the sample width, the sample duty cycle, the burst width and/or the burst duty cycle by using the feedback from the output of the bandwidth limiting unit 142.

According to still another embodiment, the feedback controller 125 is, inter alia, responsive to the changes of the sample modulation frequency and burst modulation frequency at the outputs of the amplifier (of the bandwidth limiting unit 142), the low pass filter (144 in FIG. 3B) and/or the band pass filter (145 in FIG. 3C). In this case, the feedback controller 125 is configured to generate frequency control signals in order to match the frequency characteristics of the amplifier, the low pass filter and/or the band pass filter.

According to some embodiments, a dedicated feedback loop can be provided to the system for power saving, and thereby for extending the battery life. For this purpose, the PWM corresponding to the pulse trains can, for example, be adjusted in accordance with the measured patient heart beats frequency. In this case, the feedback controller 125 can, inter alia, be responsive to the variations of the optical pass characteristic K(t) to be measured, i.e., responsive to the time response of the blood perfused body tissue to the optical signal. In particular, when the optical pass characteristic K(t) is related to heart rate (which is indicative by the time response), the feedback controller 125 can be configured to generate a measurement time interval control signal in order to adjust the width and/or duty cycle of the trains (24 in FIG. 2B) (i.e., the duration of the measurement intervals (401 in FIG. 4B)) to the variations of the heart rate. Accordingly, the repetition rate duration of the measurement periods 401 can be increased when the heartbeat rate increases. Likewise, when heartbeat rate decreases, the repetition rate and duration of the measurement periods 401 can be decreased, thus further saving the consumption energy.

In operation, the vital sign optic measurement system described above should be placed against an anatomical location of the user's body (e.g., a finger, forehead, ear pinna or an earlobe, etc.) with the blood perfused body tissue. Since the system of the present application can operate with the light reflected or scattered from the blood perfused body tissue, then it generally can be simply attached to the skin of the user via adhesives.

According to an embodiment, the vital sign measurement system can include a fixation device (not shown) that can be placed against the body part with the blood perfused body tissue. The fixation device can be any structure adapted to hold and position the vital sign measurement system or a portion thereof adjacent to an anatomical location of a user such that the optic measurement system can, for example, detect a heart rate. The fixation device can hold the optic measurement system adjacent to an anatomical location of a user at a predetermined fixation pressure or at an adjustable sensor fixation pressure. For example, the fixation device can be an adhesive bandage or a cuff (e.g., an elastic cuff or an inflatable cuff). In some implementations, the fixation device can be an inflatable cuff having an inflatable bladder that is pneumatically connected to a pump (not shown).

Generally, the fixation device can be applied to any portion of a user's body with the blood perfused body tissue. According to one embodiment, the fixation device can be positioned on an upper arm (above a user's elbow) so that the optic measurement system can sense blood movement corresponding to an arterial pulse in the brachial artery.

According to one embodiment, the fixation device can also be adapted for placement on the wrist so that the optical measurement system can sense blood movement corresponding to an arterial pulse in the radial artery. The fixation device can also be positioned on a leg (e.g., at the ankle to detect pulses in an artery), the neck, or any other part of the body where an arterial pulse can be detected.

Since the measuring probe of the present application can be miniature, the fixation device can include an ear wearable hook designed to set around the user's ear and hold the measuring probe. The receiver can, for example, to capture the signal scattered in the region of superfivial artery and vein near ear.

According to an embodiment, the vital sign measurement system can be associated with an ear piece of a music player (e.g., iPod, mp3, mp4, etc.) and plugged into the ear canal (external auditory meatus). In this case, the user may concurrently measure vital signs as well as listening the music played in the user's music player. When desired, the user may also hear a report of the vital signs measurements.

The vital sign measurement system deployed on the ear pinna or into the ear canal is more comfortable for the user than the systems arranged on the body trunk and limbs, since the measuring probe does not restrict the mobility of the user. This feature is important for the users involved in sport activities, such as jogging, athletic training or other physical exercising.

Those skilled in the art to which the present invention pertains, can appreciate that while the present invention has been described in terms of preferred embodiments, the concept upon which this disclosure is based may readily be utilized as a basis for the designing of other structures, systems and processes for carrying out the several purposes of the present invention.

Although only one optical transmitter 13 is shown in FIG. 1, when desired, the measuring probe of the vital sign measuring system can include a plurality of transmitters, each having one or more optical emitters, which in turn include one or more light sources. Using multiple transmitters/emitters/light sources can result in a lower sensitivity of the system to changes in orientation or position of the transmitters and receivers, as there will be a higher chance that the transmitter and at least one of the optical detectors are positioned properly for capturing the transmitted or reflected light.

Although only one optical emitter 131 is shown in FIG. 1, when desired, the measuring system can comprise a plurality of the receivers 131 each having one or more optical detectors. Using multiple receivers/detectors allows selection of the appropriate receiver that receives the best quality signal. Moreover, a several receivers can be used for signal correlation, in order to extract higher quality signals compared to using just one receiver. It should be understood that when a plurality of optical emitters operating at different wavelengths is used, they can be activated either simultaneously or consequently.

In a further embodiment, the control system 12 includes a plurality Pulse Width Modulators 121, each Pulse Width Modulators can be associated with the corresponding optical transmitter to provide its operation at a different frequency, duty cycle and/or light wavelength. It should be noted that using different or independent frequency, duty cycle or light wavelength for each optical transmitter allows the receiver to distinguish which transmitter's signal it receives. This provision can also facilitate the retrieval of information about the transmission channel.

It should be noted that since the Pulse Width Modulation includes more than one type of modulation, for example, in the scheme when the pulse width and burst width are modulated, the additional low pass filter 144 of the bandwidth limiting unit 142 in FIG. 2B can, for example, be with a corner frequency lower than the frequency of the repetitive bursts. This provision ensures that the signal components relating to the bursts modulation are removed from the signal.

Also, it is to be understood that the phraseology and terminology employed herein are for the purpose of description and should not be regarded as limiting.

Finally, it should be noted that the word "comprising" as used throughout the appended claims is to be interpreted to mean "including but not limited to".

It is important, therefore, that the scope of the invention is not construed as being limited by the illustrative embodiments set forth herein. Other variations are possible within the scope of the present invention as defined in the appended claims. Other combinations and sub-combinations of features, functions, elements and/or properties may be claimed through amendment of the present claims or presentation of new claims in this or a related application. Such amended or new claims, whether they are directed to different combinations or directed to the same combinations, whether different, broader, narrower or equal in scope to the original claims, are also regarded as included within the subject matter of the present description.

What is claimed is:

1. A system for optical measuring at least one vital sign of a human, the system comprising:
   (a) an optical transmitter including:
      an optical emitter configured for generating and applying a pulse width modulated optical signal to a measurement location in a blood perfused body tissue of the human, and
      an optical signal driver including a pulse generator coupled to the optical emitter and configured for generating a series of electric pulses for driving the optical emitter by turning the optical emitter "on" or "off", thereby to provide pulse width modulated optical signal;
      wherein the optical emitter comprises at least one light source;
   (b) an optical receiver including:
      an optical detector configured for receiving light originated back from at least a portion of the measurement location and generating a photocurrent signal corresponding to a time response of the blood perfused body tissue to the pulse width modulated optical signal, the time response being indicative of the at least one vital sign, and
      a bandwidth limiting unit coupled to the optical detector, having a predetermined gain and a predetermined bandwidth and configured for generating a voltage signal from photocurrent signal, the voltage signal being amplified to a desired gain level and having a desired band width; and
   (c) a control system including:
      a pulse width modulator coupled to the optical signal driver for adjusting of the width of the electric pulses transmitted to the optical signal driver that includes at least two simultaneous pulse width modulations having different modulation frequencies; and
      a signal analyzer that includes a demodulator for processing the voltage signal from the optical receiver wherein the voltage signal is produced from the pulse width modulated optical signal that includes the at least two simultaneous pulse width modulations having different modulation frequencies;
      wherein the control system is configured for
      (i) adaptive control of the pulse width modulated optical signal emitted by the optical transmitter by adjusting at least a width of the electric pulses driving the optical emitter to maintain the optical receiver in a non-saturated dynamic range; and
      (ii) processing the voltage signal generated by the bandwidth limiting unit and determining the at least one vital sign.

2. The system of claim 1, wherein the Pulse Width Modulation optical signal has a predetermined modulation frequency.

3. The system of claim 1, wherein the Pulse Width Modulation optical signal has three different modulation frequencies.

4. The system of claim 1, wherein the series of electric pulses after the at least two Pulse Width Modulations comprises repetitive bursts of electric pulse samples, each burst having a predetermined burst duration time and a predetermined burst duty cycle, and each burst comprising a predetermined number of electric pulse samples having a predetermined sample width and a predetermined sample duty cycle.

5. The system of claim 3, wherein the series of electric pulses after the three Pulse Width Modulations comprises repetitive trains of bursts of electric pulse samples, each train of the bursts has a predetermined train duration time and train duty cycle and comprises a predetermined number of bursts having a predetermined burst duration time and a predetermined burst duty cycle, and each burst comprising a predetermined number of electric pulse samples having a predetermined sample width and a predetermined sample duty cycle.

6. The system of claim 1, wherein the at least one light source operates at a wavelength in the range of 620 nm-1000 nm.

7. The system of claim 1, wherein the optical transmitter comprises a plurality of optical emitters activated either simultaneously or consequently.

8. The system of claim 1, wherein the optical detector comprises at least one photodiode.

9. The system of claim 1, wherein the bandwidth limiting unit has a bandwidth with a corner frequency below the highest Pulse Width Modulation frequency.

10. The system of claim 1, wherein the bandwidth limiting unit includes a transimpedance amplifier configured for amplifying and low pass filtering the photocurrent signal.

11. The system of claim 10, wherein the transimpedance amplifier includes an operational amplifier.

12. The system of claim 10, wherein the bandwidth limiting unit includes an additional low pass filter arranged downstream and coupled to the transimpedance amplifier.

13. The system of claim 12, wherein a cut-off frequency of the additional low pass filter is positioned between a frequency of the variation of the measured vital sign and a highest frequency of the Pulse Width Modulator.

14. The system of claim 10, wherein the bandwidth limiting unit includes a band pass filter arranged downstream and coupled to the transimpedance amplifier.

15. The system of claim 14, wherein the band pass filter has a center frequency equal to a second frequency of the at least two Pulse Width Modulations that is lower than the highest frequency.

16. The system of claim 1, wherein the signal analyzer includes a demodulator configured for processing the voltage signal generated by the bandwidth limiting unit for determining the at least one vital sign.

17. The system of claim 16, wherein the demodulator is a digital demodulator including A/D converter configured for converting the voltage signal generated by the bandwidth limiting unit from an analog form to a digital sampled form.

18. The system of claim 16, wherein the demodulator is an analog demodulator.

19. The system of claim 1, wherein the control unit comprises a feedback controller coupled to the bandwidth limiting unit and to the Pulse Width Modulator.

20. The system of claim 19, wherein the feedback controller is (i) responsive to changes in a signal amplitude at an output of an amplifier of the bandwidth limiting unit, and (ii) configured to generate an amplifier gain control signal configured for controlling operation of the Pulse Width Modulator by adjusting at least the width of the electric pulses to maintain a gain level obtained at the output of the amplifier within an optimal range for operation of the amplifier.

21. The system of claim 19, wherein the feedback controller is (i) responsive to changes in a signal amplitude at an output of a band pass filter of the bandwidth limiting unit, and (ii) configured to generate a filter control signal configured for controlling operation of the Pulse Width Modulator by adjusting the width of the electric pulses to maintain the signal amplitude at the output of the band pass filter within an optimal range for operation of the band pass filter.

22. The system of claim 19, wherein the feedback controller is (i) responsive to changes of at least one modulation frequency of the Pulse Width Modulated optical output at an output of at least one unit of the bandwidth limiting unit selected from an amplifier, a low pass filter and a band pass filter; and (ii) configured to generate frequency control signals in order to match the frequency characteristics of the amplifier, the low pass filter and/or the band pass filter.

23. The system of claim 19, wherein the feedback controller is (i) responsive to changes in a signal amplitude at an input of the demodulator, and (ii) configured to generate a detector control signal configured for controlling operation of the Pulse Width Modulator by adjusting the width of the electric pulses to maintain the demodulator within an optimal dynamic range for operation of the demodulator.

24. The system of claim 5, comprising a feedback controller coupled to the bandwidth limiting unit and to the Pulse Width Modulator, wherein the feedback controller is (i) responsive to the time response of the blood perfused body tissue to the optical signal, and (ii) configured to generate a measurement time interval control signal in order to adjust at least one modulation parameter selected from the train duration time and the train duty cycle to the variations of a heart rate of the human.

25. The system of claim 1, wherein the at least one vital sign of the human is selected from the list including a heart rate, a heart rate variability, an oxygen saturation, and a total blood hemoglobin.

26. A method for optical measuring at least one vital sign of a human, the method comprising:
  generating a Pulse Width Modulated (PWM) optical signal that includes at least two simultaneous pulse width modulations having different modulation frequencies and, adjusting at least a pulse width of the PWM optical signal;
  applying the PWM optical signal to a measurement location in a blood perfused body tissue of the human;
  receiving light originated back from at least a portion of the measurement location and generating a photo current signal corresponding to a time response of the blood perfused body tissue to the PWM optical signal, the time response being indicative of the at least one vital sign;
  generating a voltage signal from the photo current signal;
  processing the voltage signal by demodulating the voltage signal produced from the PWM optical signal that includes the at least two simultaneous pulse width modulations having different modulation frequencies; and
  determining the at least one vital sign from the voltage signal after demodulation.

27. The method of claim 26, wherein the Pulse Width Modulated optical output includes three Pulse Width Modulations having three different modulation frequencies.

28. The method of claim 26, wherein the generating of the voltage signal includes amplifying the voltage signal to a desired gain level and filtering the voltage signal to a desired band width.

29. The method of claim 26, wherein the processing of the voltage signal includes:
  converting the voltage signal from an analog form to a digital sampled form; for several periods of the Pulse Width Modulation having a lower modulation frequency than the highest modulation frequency, calculating root mean square values of measured amplitudes of samples of the sampled voltage signal located in each period of the Pulse Width Modulation having the highest modulation frequency;

executing a discrete Fourier transform of the root mean square values over the several periods; and determining a major harmonic of the variations of the root mean square values.

30. The method of claim 29, wherein the processing is carried out for a measurement at a wavelength corresponding to the red to near infrared spectral range, thereby obtaining a heart rate of the human indicated by the major harmonic.

31. The method of claim 29, wherein the processing is carried out for a measurement at two different wavelengths in the red band of light and in the infrared band of light, correspondingly.

32. The method of claim 31, comprising calculating a ratio of predetermined functions of the magnitudes of the major Fourier component of the root mean square values over the several periods for the two various wavelengths, thereby obtaining a blood oxygen saturation rate of the human.

33. The method of claim 27, wherein the generating of the optical Pulse Width Modulated (PWM) signal is carried out only during measurements intervals defined by the lowest modulation frequency of the three Pulse Width Modulations.

34. The method of claim 27, comprising adjusting at least a duty cycle of at least one modulation of the at least three Pulse Width Modulations.

35. The method of claim 34, comprising providing a feedback closed loop control configured for the adjusting of the duty cycle of the at least one modulation of the at least three Pulse Width Modulations.

* * * * *